United States Patent [19]

Sekii et al.

[11] Patent Number: 5,046,505

[45] Date of Patent: Sep. 10, 1991

[54] APPARATUS AND METHOD FOR MEASURING CARDIAC OUTPUT

[75] Inventors: Shigekazu Sekii; Makoto Ikeda; Kouji Tsuchida, all of Fuji, Japan

[73] Assignee: Terumo Kabushiki Kaisha, Tokyo, Japan

[21] Appl. No.: 415,298

[22] PCT Filed: Mar. 4, 1988

[86] PCT No.: PCT/JP88/00239

§ 371 Date: Sep. 5, 1989

§ 102(e) Date: Sep. 5, 1989

[87] PCT Pub. No.: WO88/06426

PCT Pub. Date: Sep. 7, 1988

[30] Foreign Application Priority Data

| Mar. 5, 1987 | [JP] | Japan | 62-48821 |
| Mar. 5, 1987 | [JP] | Japan | 62-48822 |
| Mar. 5, 1987 | [JP] | Japan | 62-48823 |
| Mar. 5, 1987 | [JP] | Japan | 62-48824 |
| Mar. 5, 1987 | [JP] | Japan | 62-48825 |
| Mar. 5, 1987 | [JP] | Japan | 62-48826 |

[51] Int. Cl.$^5$ .............................................. A61B 5/028
[52] U.S. Cl. .................................................. 128/713
[58] Field of Search .............. 128/691, 713, 692, 736

[56] References Cited

U.S. PATENT DOCUMENTS

| 3,438,253 | 4/1969 | Kuether | 73/204.15 |
| 3,595,079 | 7/1971 | Grahn | 73/204.15 |
| 3,678,922 | 7/1972 | Philips | 128/692 |
| 3,789,831 | 2/1974 | Kopaniky | 128/692 |
| 3,820,530 | 6/1974 | Gilford | 128/713 |
| 3,995,623 | 12/1976 | Blake | 128/642 |
| 4,004,576 | 1/1977 | Gähwiler | 128/713 |
| 4,035,622 | 7/1977 | Obermajer | 128/713 |
| 4,230,126 | 10/1980 | Elings | 128/671 |
| 4,240,441 | 12/1980 | Khalil | 128/692 |
| 4,380,237 | 4/1983 | Newbower | 128/693 |
| 4,502,488 | 3/1985 | Degironimo | 128/692 |
| 4,542,748 | 9/1985 | Roy | 128/713 |
| 4,572,206 | 2/1986 | Geddes | 128/692 |
| 4,595,015 | 6/1986 | Jansen | 128/713 |
| 4,621,646 | 11/1986 | Bryant | 128/692 |
| 4,632,125 | 12/1986 | Webler | 128/692 |
| 4,685,470 | 8/1987 | Sekii | 128/692 |
| 4,841,981 | 6/1989 | Tanabe | 128/692 |

OTHER PUBLICATIONS

Dew, Robert B., "Personal Computer System for Automatic Coronary Venous Flow Measurement," *Computer Applications in Medical Care*, IEEE Computer Society, pp. 41-44.

(List continued on next page.)

Primary Examiner—William E. Kamm
Assistant Examiner—Kevin Pontius
Attorney, Agent, or Firm—Staas & Halsey

[57] ABSTRACT

Disclosed is an apparatus for measuring a cardiac output on the basis of a dilution method. The measuring apparatus includes a switch for inputting a parameter or the like of an outer diameter or the like of a catheter, a probe for detecting the temperature of an injectate into the blood vessel by the dilution method, a switch for manually inputting the injectate temperature, a circuit for detecting non-connection of the probe, a circuit for selectively switching over the manually input injectate temperature data and the detected injectate temperature data, a catheter having an opening through which the indicator is injected, a first thermistor for measuring the temperature of the blood diluted by the indicator, and a second thermistor for detecting its heat balanced temperature obtained by being cooled by the blood, a circuit for detecting a variation in the blood temperature detected by the first thermistor and starting the integration of the area of a dilution curve in accordance with the theory of the dilution method, a circuit for continuously operating a cardiac output from the heat balanced temperature detected by the second thermistor, and a recording device for recording the continuously obtained cardiac outputs in the order in which they are operated.

21 Claims, 22 Drawing Sheets

OTHER PUBLICATIONS

European Search Report No. EP 87 10 3083, The Hague, 13-04-88.
PCT International Application No. PCT/US88/00300; Filed Feb. 27, 1984.
Proceedings of the Ninth Annual Symposium on Computer Applications In Medical Care, Baltimore, Maryland, 10th-13th Nov. 1985, pp. 41-44; R. B. Dew.
European Patent Application No. 85114716.5 (Terumo K.K.), Publication No. 0 182 363, Publication Date: 05/28/86.
Thermal Method for Continuous Blood-Velocity Measurement in Large Blood Vessels, and Cardiac-Output Determination, vol. 11, No. 2, Mar. 1973, pp. 201-205.

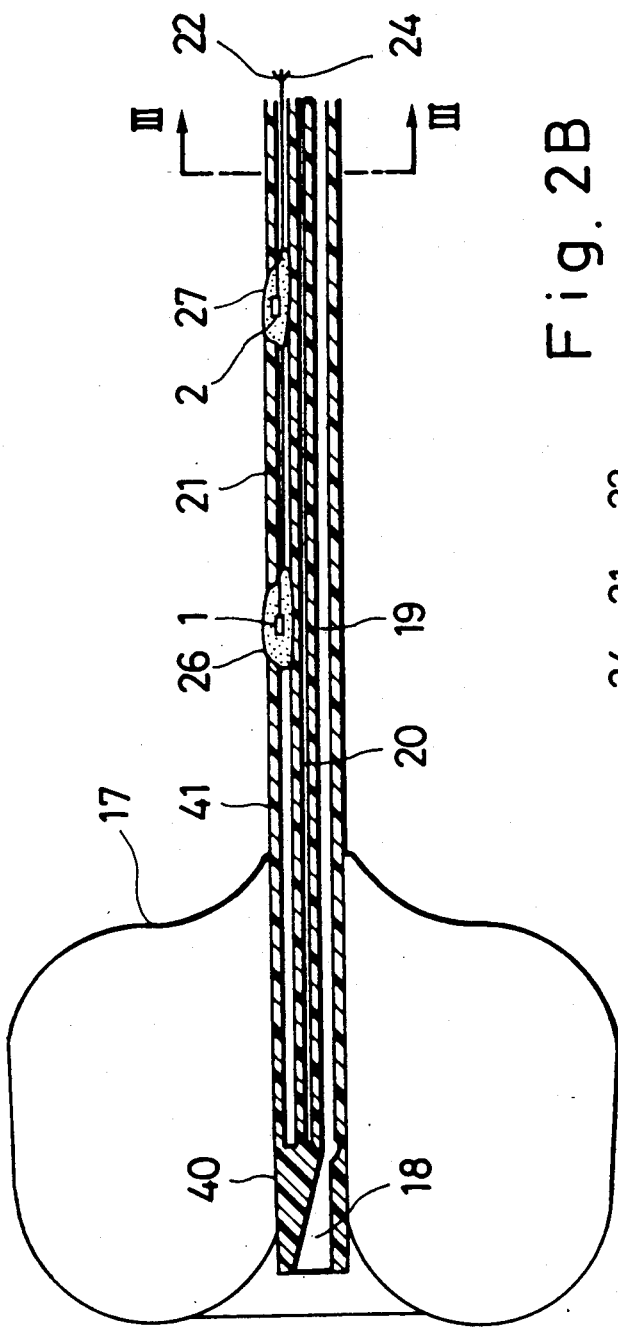
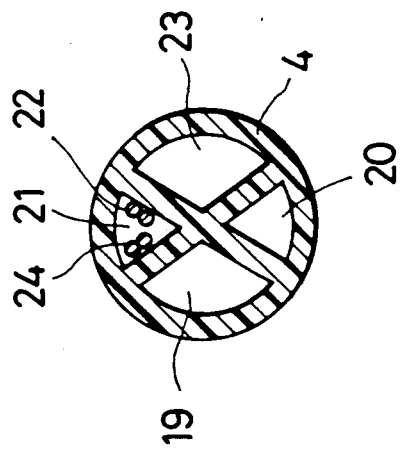
Fig. 2B
Fig. 2C

```
86-11-18              86-11-18              86-11-18              86-11-18
13:14                 13:20                 13:23                 13:29
CO  4.70  L/min       CO  4.90. L/min       CO  4.82  L/min       CO  4.65  L/min
BSA 1.11  M2          BSA 1.11  M2          BSA 1.11  M2          BSA 1.11  M2
CI  4.23  L/min M2    CI  4.41  L/min/M2    CI  4.34  L/min/M2    CI  4.19  L/min/M2
BT  37.2  °C          BT  37.2  °C          BT  37.0  °C          BT  37.2  °C
CAT 5.0   Fr          CAT 5.0   Fr          CAT 5.0   Fr          CAT 5.0   Fr
IV  5     mL          IV  5     mL          IV  5     mL          IV  5     mL
IT  0.2   °C          IT  0.2   °C          IT  0.1   °C          IT  0.2   °C

ENTRY             ENTRY             ENTRY
```

Fig. 5

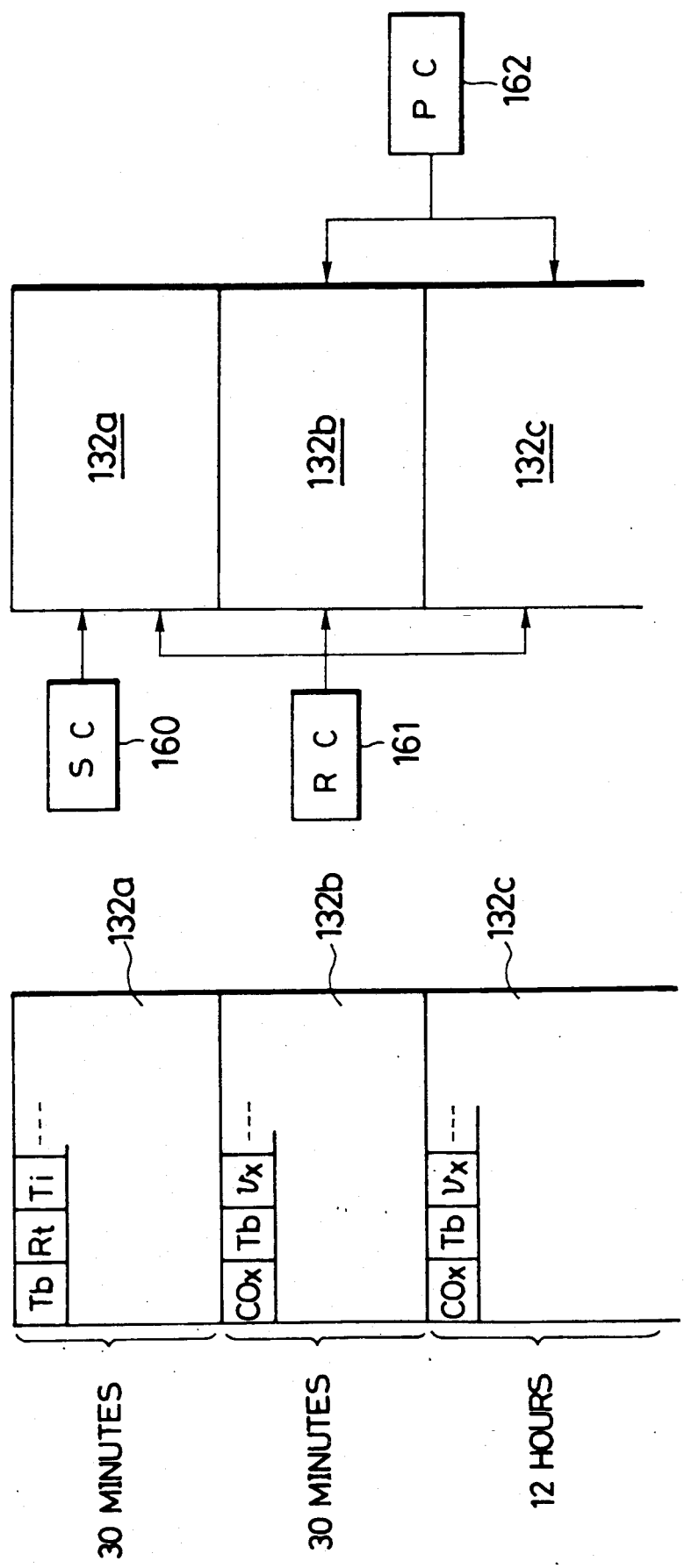

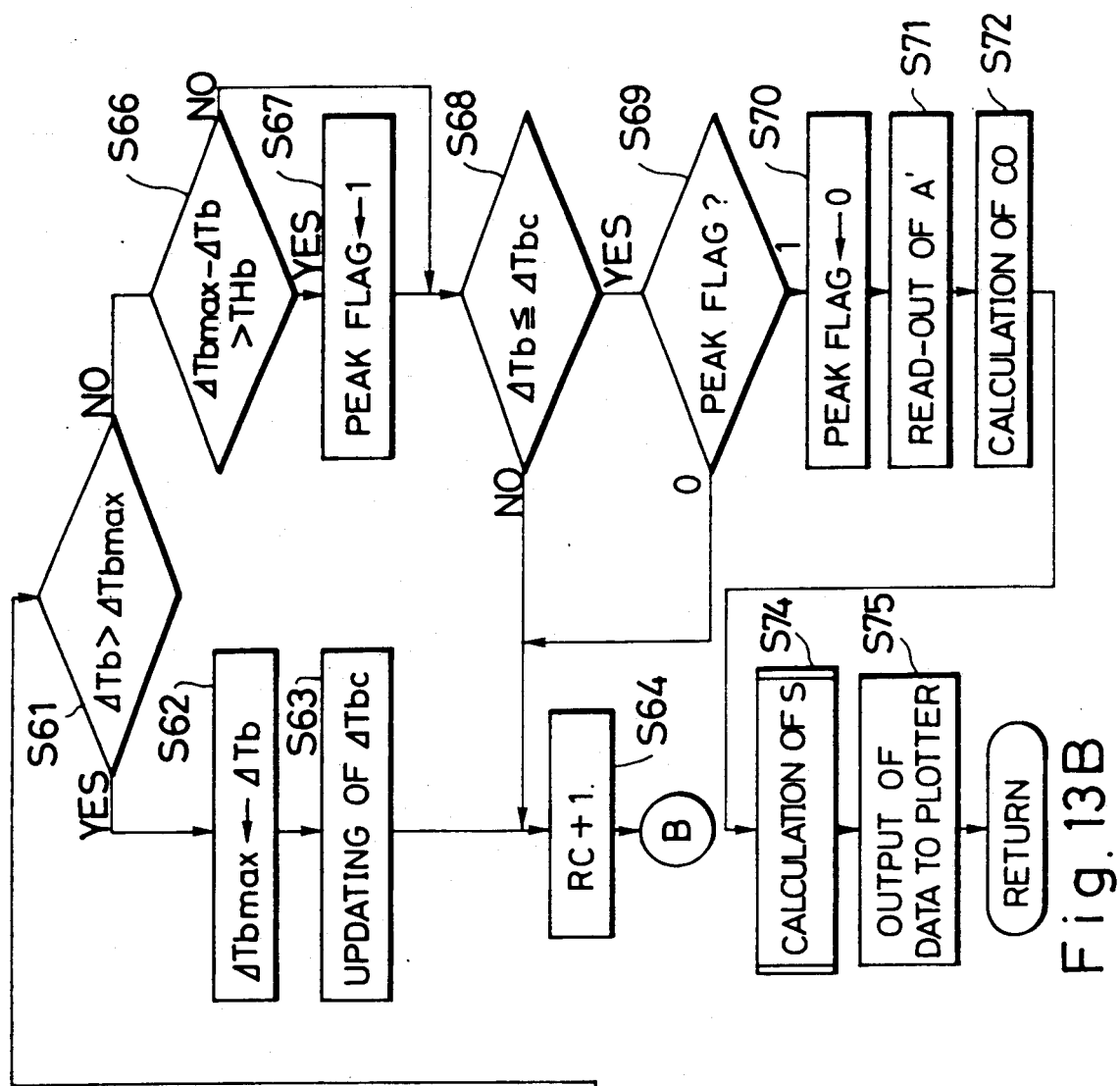
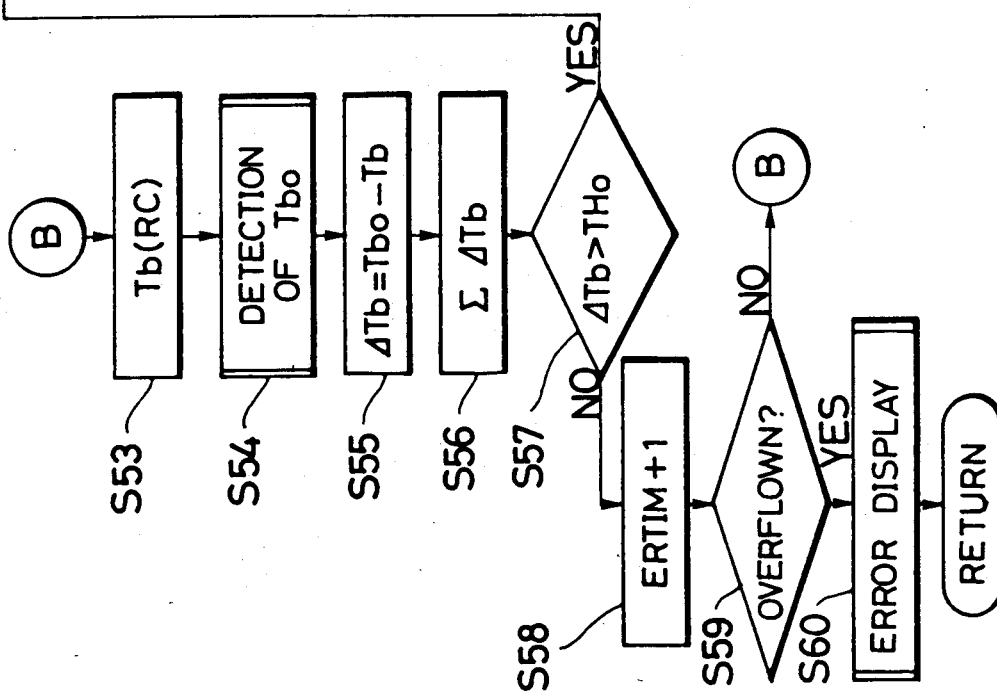
Fig. 13B

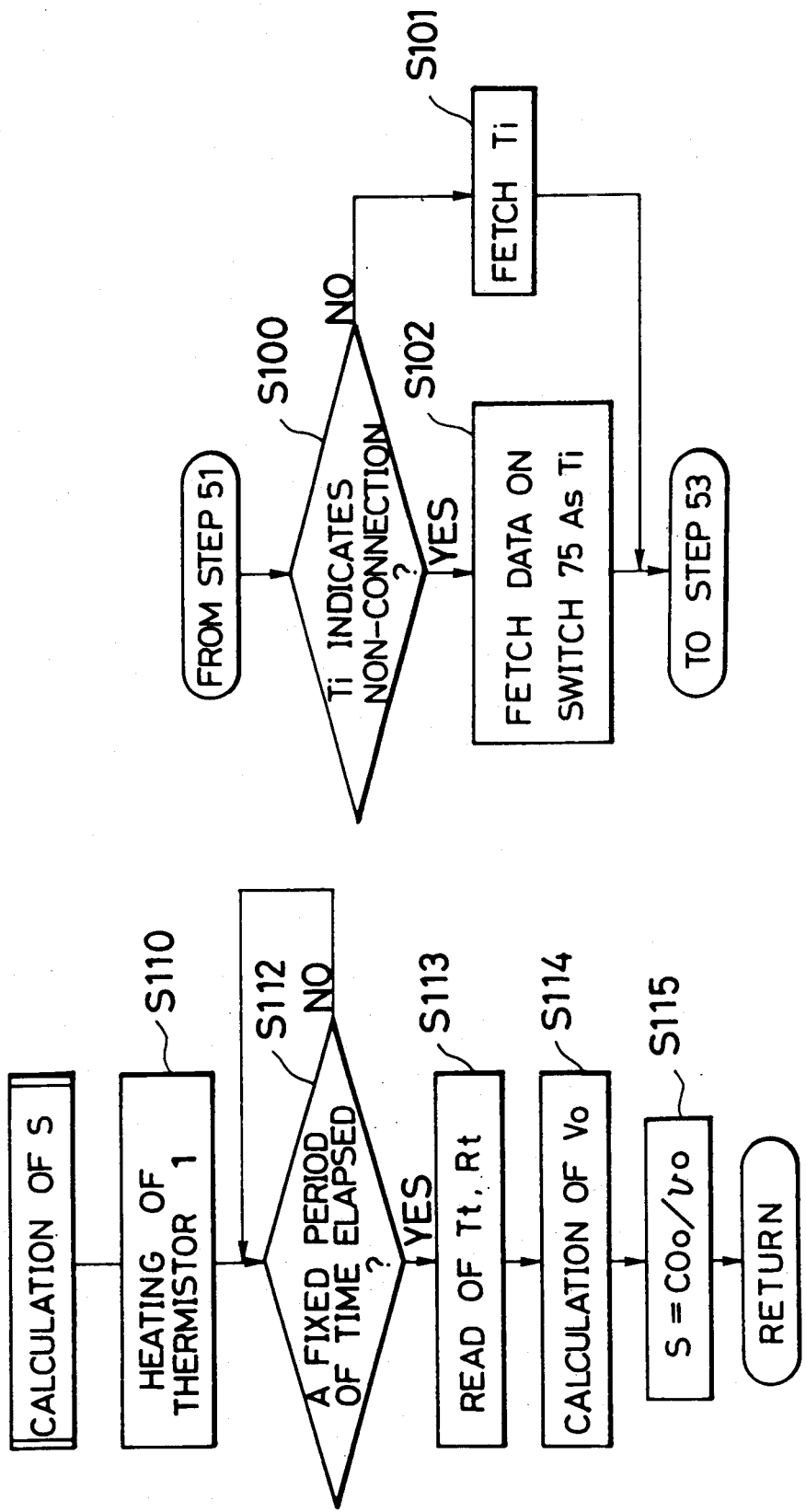

APPARATUS AND METHOD FOR MEASURING CARDIAC OUTPUT

TECHNICAL FIELD

The present invention relates to a cardiac output measuring apparatus for use in a cardiac function inspection or the like.

BACKGROUND ART

Conventionally, the measurement of cardiac output by right heart catheterization, which is performed in a cardiac function inspection, employs the indicator dilution method. This indicator dilution method is classified into three categories: the thermal dilution method in which the cardiac output is obtained by utilizing thermal diffusion, the dye dilution method in which the cardiac output is obtained utilizing variations in the illuminance which are caused by the diffusion of a dye, and the electrolyte dilution method in which the cardiac output is obtained utilizing variations in the resistance caused by the diffusion of an electrolyte. The thermal dilution method will be described below in detail.

In right heart catheterization, a catheter 4 is introduced into the body from the cervical vein, the femoral vein, the basilic vein or the like. The forward end of the catheter passes through the superior vena cava or the inferior vena cava, the right atrium and then the right ventricle, and finally reaches the pulmonary artery, as shown in FIG. 16. The catheter 25 has a injection port 26 and a thermistor 1, which are respectively positioned in the right atrium and in the pulmonary artery when the forward end of the catheter 25 is located within the pulmonary artery. When a liquid having a temperature higher or lower than that of the blood is ejected into the right atrium from the injection port 26, it is diffused in the right atrium and the right ventricle and is diluted by the blood. The temperature of the liquid diluted is detected by the thermistor 27 located within the pulmonary artery to obtain a dilution curve of the temperature detected (which is a graph of the variations in the temperature with time), and the cardiac output is calculated from the area or the like of that dilution curve by the Stewart Hamilton Method using the following equation (1).

$$CO = \frac{Si \cdot Ci \cdot (Tb - Ti) Vi}{Sb \cdot Cb \cdot \int_0^\infty \Delta Tb \, dt} \quad (1)$$

where CO is the cardiac output, Si is the specific gravity of the injectate, Ci is the specific heat of the injectate, Vi is the volume of injectate, Ti is the temperature of the injectate, Tb is the temperature of the blood, Sb is the specific gravity of the blood, Cb is the specific heat of the blood, and $$\int_0^\infty \Delta Tb \, dt$$

is the area of the thermal dilution curve. Calculation of the cardiac output by the Stewart Hamilton Method is known as being relatively accurate. Cardiac output measuring apparatuses which perform measurement on the basis of this method have been available.

However, such a conventional cardiac output measuring apparatus requires a relatively high degree of skill and troublesome operation. Hence, there has been a demand for an apparatus which is simple and easy to use and which ensures accurate measurement. The inventors of this application have studied the measurement of the cardiac output by the dilution method, in particular, the measurement of the cardiac output by the thermal dilution method, and have found the following five problems with the conventional measuring apparatuses.

(i): As can be seen from the above equation, in the thermal dilution method, the volume of the injectate and the temperature thereof greatly affect the accuracy of the calculation. Normally, after the temperature Ti of the liquid has been accurately measured by a thermistor or the like, the catheter 26 is primed and the indicator is then injected into the blood vessel. However, the indicator may be cooled or heated by the body temperature before it enters the blood vessel, causing measurement errors. More specifically, when the indicator having a temperature set to the correct value is injected, the temperature of the liquid is raised or lowered by the body temperature from its initial value at the beginning of the injection, the liquid having substantially its original temperature being injected a certain period of time after the injection has started. This can be the cause of measurement errors, because the total heat capacity of the injectate into the blood vessel is an unknown value. The heat capacity is mainly determined by the capacity of the catheter, the volume Vi of the liquid to be injected and the injectate temperature Ti. The capacity of the catheter is a factor ignored in the Stewart Hamilton Method. Generally, the capacity of the catheter is determined in accordance with the outer diameter (French size) of the catheter. Conventionally, the heat capacity is estimated using the volume of the injectate, the catheter size and so on, and a correction constant is obtained by comparing the experimentally obtained cardiac outputs with these estimated values. A more accurate cardiac output, which is not affected by the residual liquid, is obtained by utilizing this correction constant.

However, the aforementioned correction constant which is conventionally obtained using the volume of the liquid remaining in the catheter is a numeric value which is meaningless to the operator, and this renders it liable to be erroneously calculated or erroneously input to the measuring apparatus.

(ii): In the above-described measurement of the cardiac output on the basis of the thermal dilution method which is expressed by Equation (1), it is essential to accurately measure the temperature Ti of the indicator to be injected, because the temperature Ti not only appears in the term (Tb-Ti) in the above-described equation and but also has a relation with the heat capacity of the residual liquid which can be the cause of measurement errors, as described in (i).

Generally, the indicator is immersed in an ice-cooled or warmed solution whose temperature is kept constant. The temperature of the ice cooled or warmed solution in which the indicator is immersed may therefore be regarded as the temperature T1 of the indicator in a case where a skillful operator handles it or in a case where the desired cardiac output value is not an absolutely precise one. However, conventionally, measurement of the injectate temperature is performed for each measurement. This makes the cardiac output measurement inefficient.

In other words, in the cardiac output measurement apparatus which employs the dilution method, it is anticipated that, when it is determined that the operator is not going to perform measurement of data or when the apparatus detects an instruction of non-measurement of data, the manually preset data is used.

(iii): As can be seen in the graph in FIG. 17, sampling of the blood data required for the calculation of the area (integration) of the dilution curve has to be started within a certain period of time after the injection of the indicator. Starting of the calculation of the integration a long time after the blood temperature has dropped may cause calculation errors. However, conventionally, the indicator injection side may be apart from the measuring apparatus installation side. In that case, one of the two operators who is in charge of the injection of the liquid gives an instruction to the other after the liquid has been injected, and the other operator starts measurement, i.e., starts integration. In consequence, there has been always the possibility of measurement errors. In a case where the single operator takes care of both operations, he or she must do them quickly in a short period of time.

Not only the thermal dilution method but also the other indicator dilution methods involve these measurement errors and the troublesome operation.

(iv): In the above-described cardiac output measurement method which employs the thermal dilution method or the other indicator dilution methods, measurement of the cardiac output is performed intermittently each time the injector is injected. It is therefore impossible to continuously measure the cardiac output. If measurement is performed frequently, the total volume of the injectate increases, increasing the burden on the examinee and increasing the risk that the examinee may be infected during the liquid injection.

In order to eliminate the disadvantages experienced by the conventional cardiac output measurement which is based on the indicator dilution method, in particular, the thermal dilution method and which is only capable of intermittent measurement, the present inventors have proposed under Japanese Application No. 59-244586 (in the specification of Japanese Patent Laid-Open No. 61-125329) an improved cardiac output measuring apparatus which is capable of continuously measuring the cardiac output. This continuously measuring apparatus involves the measurement of the cardiac output over a long period of time and continuous recording of the cardiac output.

(v): Subject matter of Japanese Application No. 59-244586 is to obtain the relation between the cardiac output and the blood flow velocity which are actually obtained in the measurement based on the thermal dilution method and to operate the cardiac output thereafter from the thus-obtained relation and the blood flow velocity actually measured. Because the cardiac output and the blood flow velocity have a certain relation, if the blood flow velocity obtained is not an absolute one, relative changes in the cardiac output can be obtained using that relation.

DISCLOSURE OF INVENTION

In view of the aforementioned problems of the prior art, an object of the present invention is to provide a cardiac output measuring apparatus which enables the correction term relating to the volume of indicator remaining in a catheter that can be the cause of the measurement errors to be numerically input as a value realistic to an operator so as to ensure simple and easy operation of the apparatus.

To this end, the present invention provides an apparatus for measuring a cardiac output by the thermal dilution method which comprises an injection means for injecting an indicator into the blood vessel, a blood data detection means for outputting data on the blood which is diluted by the indicator injected, an integration means for calculating a time integration of the blood data, an input means for manually inputting a plurality of types of data on the heat capacity of the indicator injected by the injection means independently of each other, and a cardiac output operation means for operating a cardiac output from the integral value and the data on the heat capacity which is input in accordance with the thermal dilution method.

In the present invention, since the physical quantities on the heat capacity, such as the dimension of a catheter and the temperature of the indicator which affect the volume of indicator remaining in the catheter, can be input independently of each other, they are realistic to the operator, and this enables the input errors which would occur conventionally to be eliminated.

In one form of the invention, the blood data detection means includes a temperature sensor, and the blood data represents data on the temperature of the blood.

In another form of the invention, the injection means includes a catheter, and the data on the heat capacity represents the volume of indicator injected, the outer diameter of the catheter, or the temperature of the indicator. These types of data are the important factors that affect the measurement accuracy. In consequence, the cardiac output measurement operation can be made simple and the measurement accuracy can be improved by eliminating the input errors of the data.

Another object of the present invention is to provide a cardiac output measuring apparatus which enables manually preset data to be employed in place of data to be obtained by measurement when it is detected that the operator is not going to perform the measurement of that data although he or she considers it important, so as to make the operation of the apparatus simple and easy.

To this end, the present invention provides an apparatus for measuring a cardiac output by the thermal dilution method which comprises a data setting means for manually setting data on an indicator which is not yet injected into the blood vessel, a measuring means for obtaining data on an indicator which is not yet injected into the blood vessel, a blood data detection means for detecting data on the blood which is diluted by the indicator injected into the blood vessel, an integration means for integrating the blood data obtained at each time, a selection means for selecting either the data set by the setting means or the data obtained by the measuring means, and a cardiac output operation means for operating a cardiac output from the selected data and the integral value. In the present invention, when it is detected by the selection means that the operator considers it unnecessary to perform measurement of the data required for calculation, the data manually preset by means of the data setting means can be employed in place of that data, thereby making the operation of the apparatus simple.

In one form of the invention, the measuring means includes a measuring probe connected to the cardiac output measuring apparatus, and the cardiac output measuring apparatus further includes a non-connection detection means for detecting non-connection of the indicator data detection means to said cardiac output measuring apparatus. Only when the non-connection detection means detects non-connection, the selection means selects the data input from the input means as the indicator data. In this way, the measuring apparatus determines that the operator considers it unnecessary to perform measurement of data required for calculation.

In another form of the invention, the indicator data represents the temperature of the indicator.

In another form of the invention, the data setting means includes numeric input keys.

Another object of the present invention is to provide a cardiac output measuring apparatus having the automatic measurement starting function which is capable of recognizing the time at which an integration is to be started to automatically start it, which enables measurement errors to be eliminated, and which makes the operation conducted by the operator simple.

To this end, the present invention provides an apparatus for measuring a cardiac output by the dilution method which comprises a blood data detecting means for outputting data on the blood diluted by an indicator injected into the blood vessel, a variation operation means for operating variation in the blood data, a comparison means for comparing the variation operated with a predetermined value to determine whether the variation is equal to or larger than the predetermined value, an integration means for starting an integration of the blood data to be obtained at each time subsequent to the comparison when it is determined that the variation operated is equal to or larger than the predetermined value, and a cardiac output operating means for operating a cardiac output from the integral value. In the dilution method, integration of the blood data obtained at the time at which the variation in the blood data occurs and subsequent to that time is essential. In the present invention, since variation in the blood data is monitored by the comparison means, only when the variation satisfies a predetermined condition, integration starts. In consequence, an cardiac output can be obtained without requiring the operator, thereby eliminating measurement errors caused by the operator.

In one form of the invention, the blood data detection means includes a temperature sensor, and the blood data represents data on the temperature of the blood diluted by the indicator injected into the blood vessel.

In another form of the invention, the integration means includes an operation means for starting an integration of a difference between the blood data and reference blood data determined before the determination by the comparison means and for integrating the difference at each time, and a stoppage means for stopping the integration when the blood data substantially coincides with the reference blood data. In consequence, it is possible to obtain the theoretically most accurate cardiac output.

In another form of the invention, the integration means includes an operation means for staring an integration of a difference between the blood data and reference blood data determined before the determination by the comparison means and for integrating the difference at each time, a detection means for detecting a peak value of the difference, and a means for obtaining an integration period in which the integration is continued on the basis of the peak value. In consequence, the cardiac output can be measured efficiently and with a high degree of accuracy.

In another form of the invention, the variation operation means is capable of operating a difference in the moving average values of the blood data. In consequence, an integration starting point can be detected without being affected noise and with a high degree of accuracy, thus improving the accuracy with which the cardiac output can be measured.

Another object of the present invention is to provide a cardiac output measuring apparatus which is capable of continuously measuring and recording a cardiac output over a long period of time.

To this end, the present invention provides a cardiac output measuring apparatus which comprises a cardiac output measuring means for performing the measurement of a cardiac output on the basis of a dilution method at least once to obtain an initial cardiac output, a blood flow velocity measuring means for measuring a blood flow velocity in the vicinity of the portion of the blood vessel at which the cardiac output is measured by the cardiac output measuring means, a function operation means for operating a function representing the relation between the cardiac output obtained on the basis of the dilution method and a blood flow velocity obtained when the cardiac output is measured, a cardiac output operation means for continuously operating a cardiac output at individual times on the basis of the function and the blood flow velocities obtained at the times by the blood flow velocity, a memory means for storing the cardiac outputs obtained at the individual times in the order in which they are generated, and a recording means for visually and retroactively recording the cardiac outputs stored.

In one form of the invention, the dilution method is a thermal dilution method. The cardiac output measuring means includes a catheter having an opening through which the indicator is injected into the blood and a first thermistor for measuring the temperature of the blood diluted by the indicator at the downstream side of the blood vessel, and an integrating means for integrating the blood temperature data detected by the thermistor. The blood flow velocity measuring means includes a second, self-heating type thermistor provided in the vicinity of the first thermistor of the catheter. In consequence, both the data (blood temperature) required for the initial cardiac output measurement and the data (heat balanced temperature) required for continuously measuring a cardiac output can be obtained by means of one catheter, and the size of the overall apparatus can be thereby reduced.

In another form of the invention, the cardiac output measuring apparatus includes a first microprocessor for collecting data, a second microprocessor for processing data, and a communication means for exchanging data between the two microprocessors. The first microprocessor collects the blood temperature data detected by the first thermistor and the heat balanced temperature data detected by the second thermistor, and sends them to the second microprocessor by means of the communication means. The second microprocessor processes the data collected and thereby operates the initial cardiac output and the function. In consequence, the data collection and the data processing are performed in parallel by the corresponding microprocessors, and this allows accurate cardiac output data to be offered to the operator at a high speed.

In another form of the invention, the cardiac output operation means includes a means for compressing the cardiac outputs operated within a predetermined period of time, and a memory for storing the cardiac outputs compressed. The recording means is capable of recording the cardiac outputs compressed. In consequence, continuous measurement and data recording can be performed over a long period of time.

Another object of the present invention is to provide a cardiac output measuring apparatus having the function of obtaining relative changes in the cardiac output by obtaining a blood flow velocity.

To this end, the present invention provides a cardiac output measuring apparatus which comprises a blood flow velocity measuring means for measuring a blood flow velocity, an input means for inputting an arbitrary value, and a cardiac output operation means for continuously operating the relative changes in the cardiac output which occur as the time elapses from the arbitrary value and the blood flow velocity measured by the blood flow velocity measuring means at the individual times.

In one form of the invention, the arbitrary value represents a cross-sectional area of the blood vessel.

BRIEF DESCRIPTION OF THE DRAWINGS

FIG. 2B is a cross-sectional view of the essential parts of the catheter of FIG. 2A;

FIG. 2C is a cross-sectional view of the catheter of FIG. 2A, showing an opening thereof;

FIGS. 4 and 5 show the examples of the output of the results of the measurement of the cardiac output by the apparatus of FIG. 1 on the basis of the thermal dilution method;

FIGS. 10A and 10B respectively show the management of a RAM incorporated in the measuring apparatus of FIG. 1;

FIGS. 11, 13A, 13B, 14A, 14B and 15 are respectively flow charts of the control procedure of the measuring apparatus of FIG. 1;

BEST MODE FOR CARRYING OUT THE INVENTION

An embodiment of the present invention will be described below with reference to the accompanying drawings.

External View of the Apparatus

Figure 1A:
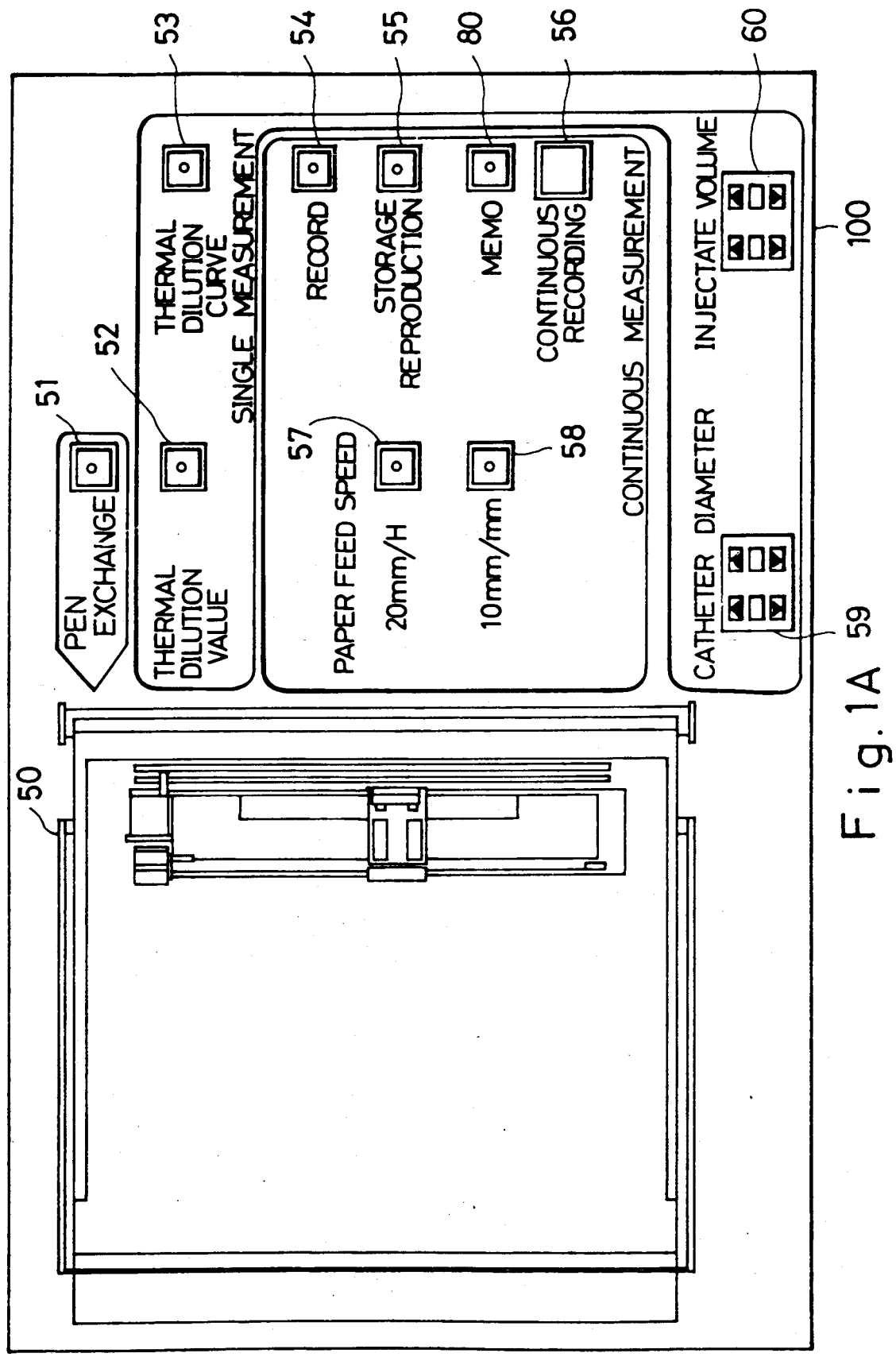
FIGS. 1A, 1B, and 1C are respectively plan, front and rear views of an embodiment of measuring apparatus according to the present invention.
Figure 1B:
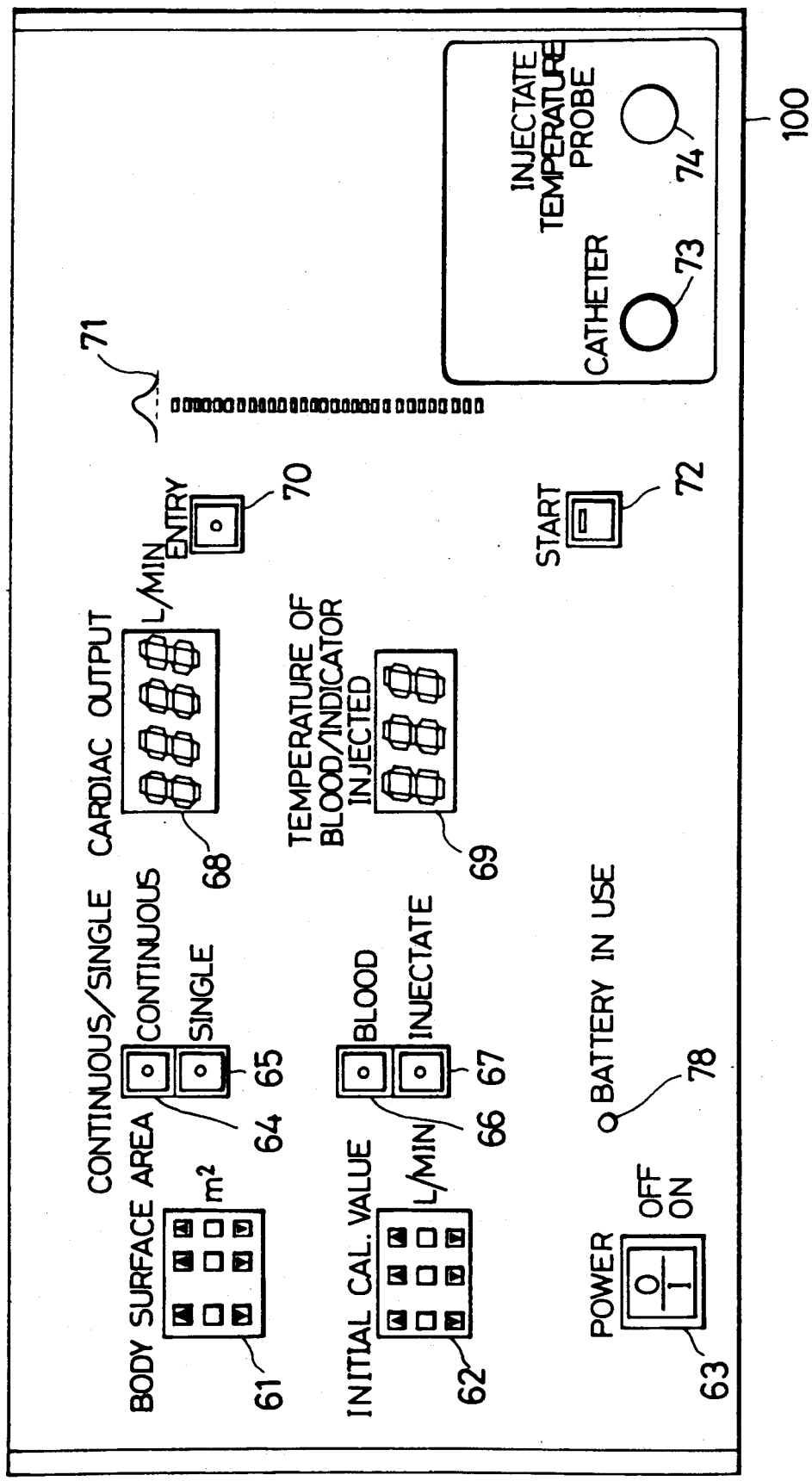
Figure 1C:
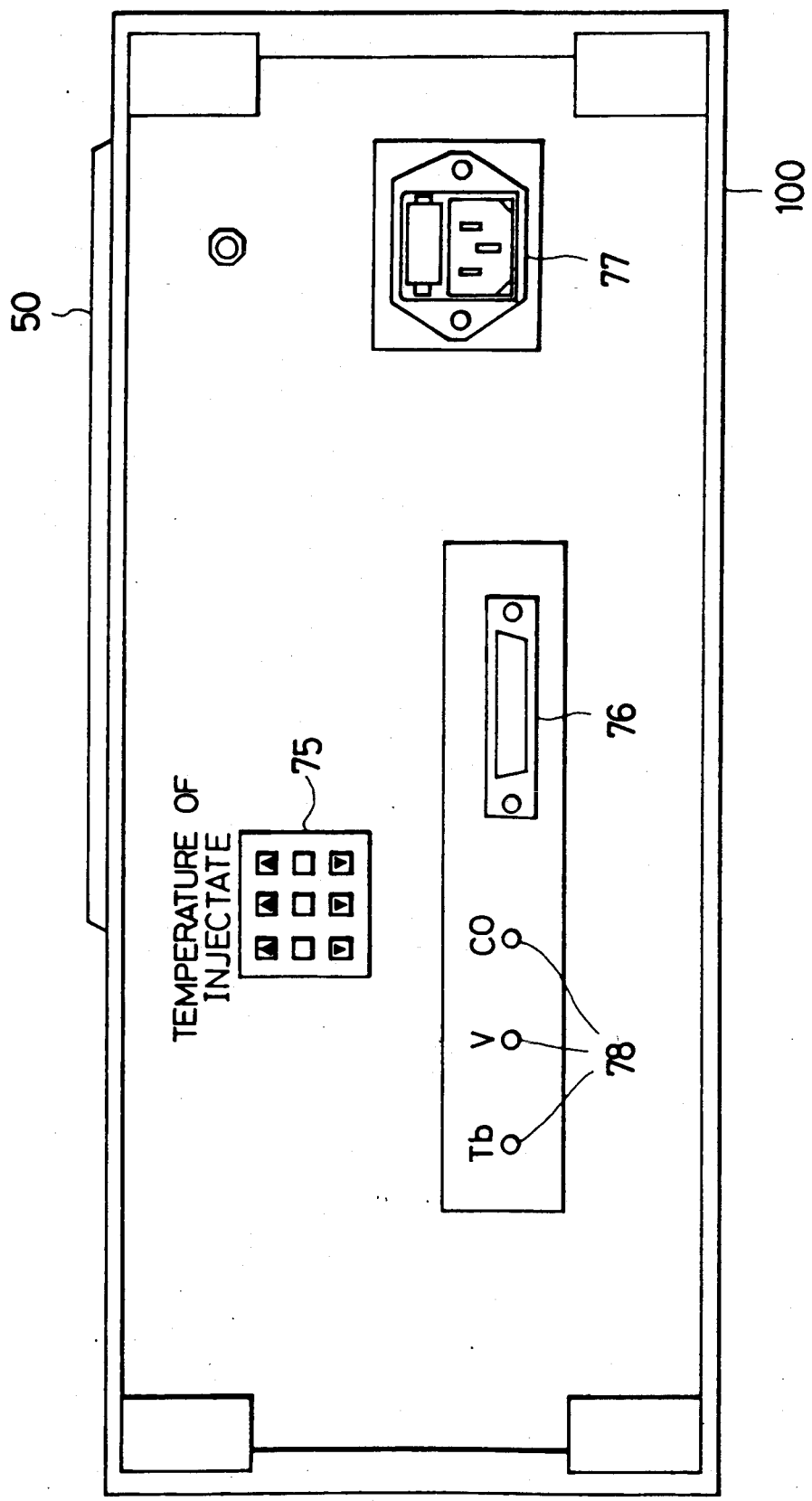
Figure 2A:
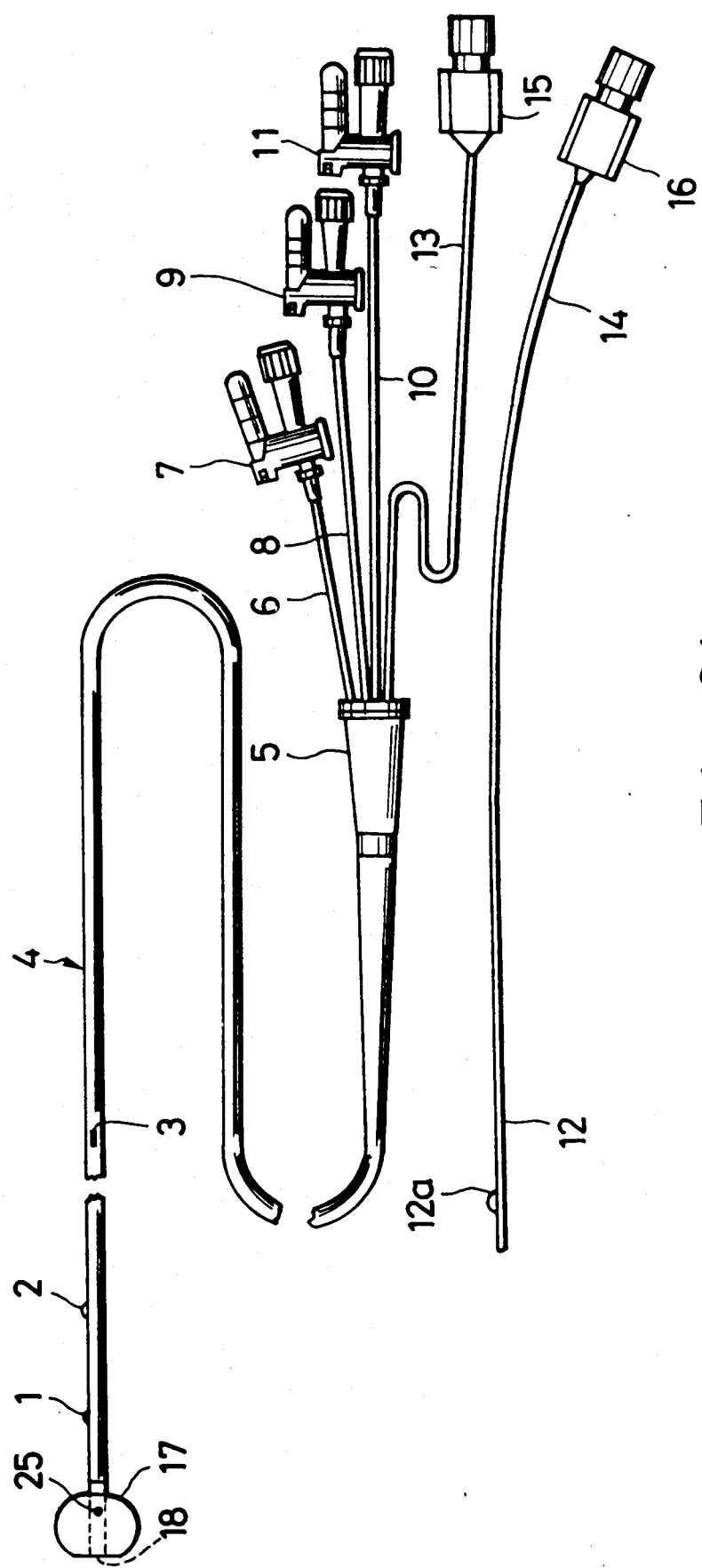
FIG. 2A is a perspective view of the entirety of a catheter employed in the measuring apparatus of FIG. 1.
Figure 3A:
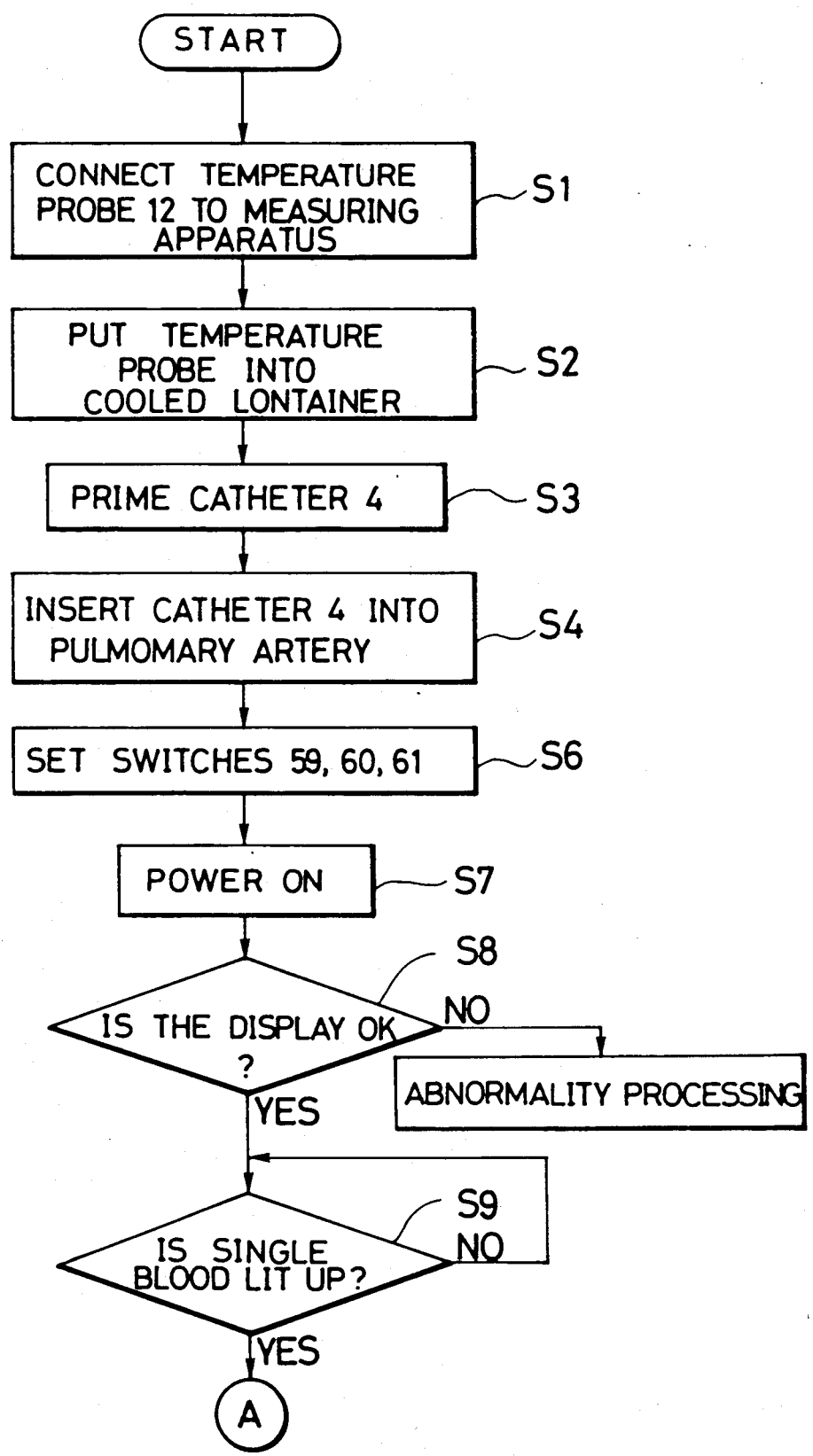
FIGS. 3A and 3B are flowcharts of the operation procedure of the measuring apparatus of FIG. 1.
Figure 3B:
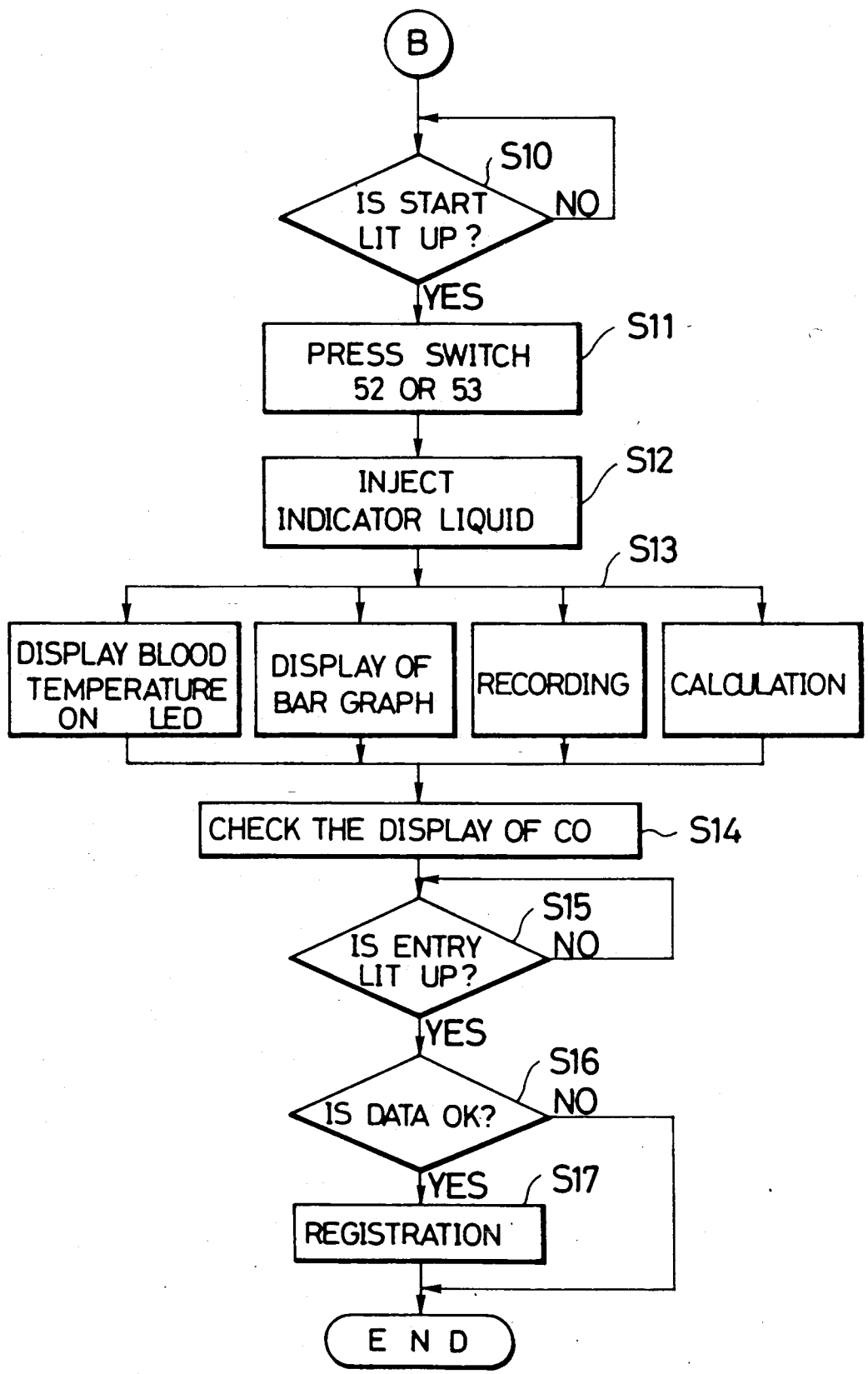

FIGS. 1A, 1B and 1C are respectively plan, front and rear views of a cardiac output continuous measuring-/recording apparatus to which the present invention is applied. FIG. 2A shows the external view of a catheter connected to the measuring apparatus of FIG. 1, FIG. 2B is a cross-section of the forward end portion of the catheter which is taken in the longitudinal direction thereof, and FIG. 2C is a cross-section of the catheter, showing openings formed in the catheter.

The measuring apparatus operates on the basis of the following principles. First, an initial cardiac output COo is measured by the indicator dilution method, such as the thermal dilution method, the electrolyte dilution method or the dye dilution method, and then the blood flow velocity Vo at the time when the cardiac output is measured is measured. Thereafter, a parameter s representing the relationship between the blood flow velocity Vo and the initial cardiac output COo (where COo=Vo·S) is obtained. After the parameter s has been obtained, the cardiac output COx (=Vx·S) at an arbitrary time is obtained from the blood flow velocity Vx actually measured at that arbitrary time and the parameter S. Any type of indicator dilution method can be employed to obtain the initial cardiac output. However, the embodiment of the present invention, which will be described below, employs the thermal dilution method.

Figure 4:
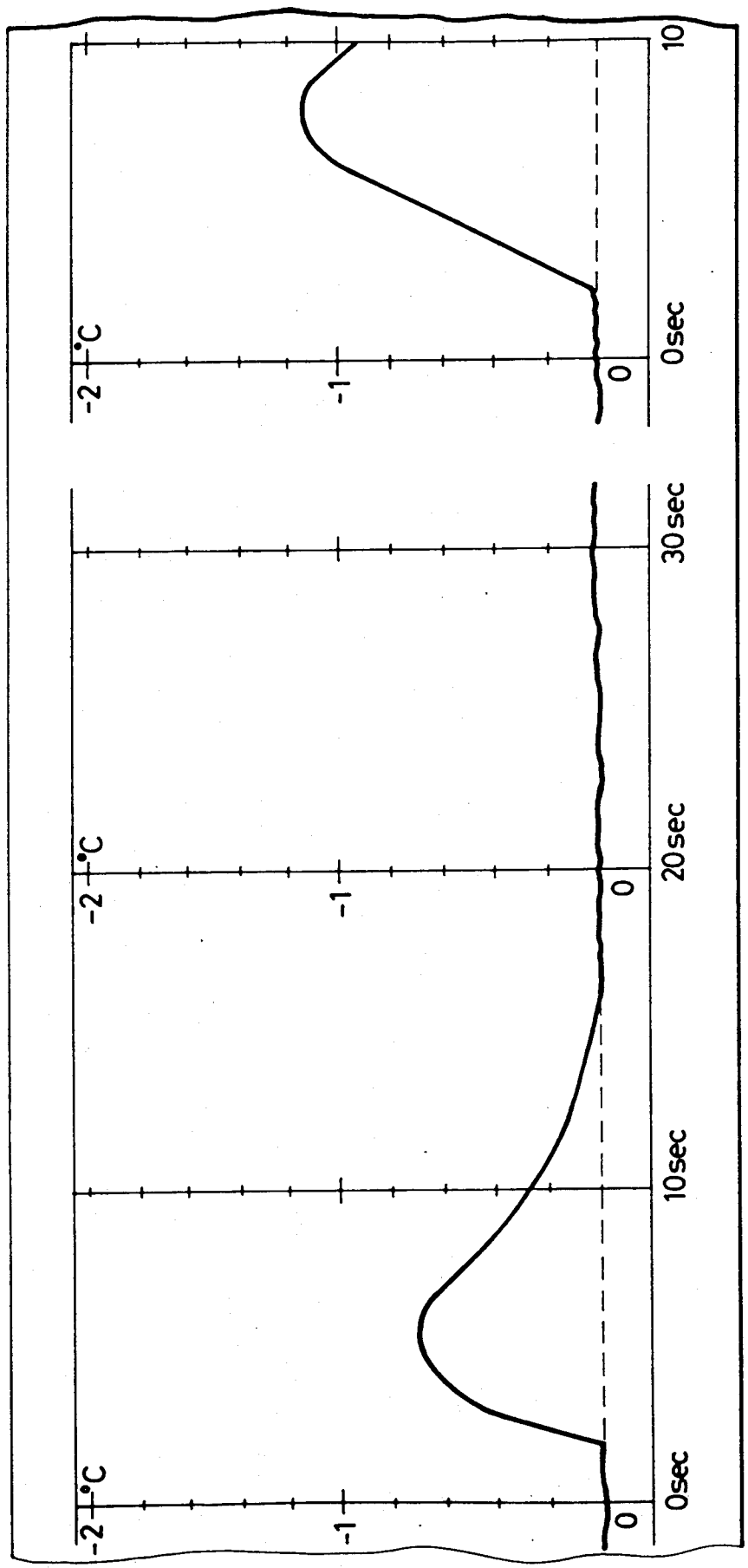

The external view of a measuring apparatus 100 shown in FIGS. 1A to 1C will be described. In FIG. 1A, a reference numeral 50 denotes a recording device, such as a plotter, which outputs the results of the measurement. Reference numerals 52 and 53 denote switches which are used to designate the form in which the initial cardiac output COo measured by the thermal dilution method is output to the plotter 50. By pressing the switch 52 marked "Thermal Dilution Value", the cardiac output CO is numerically output (as shown in FIG. 5). The switch 53 marked "Thermal Dilution Curve" is used to designate the graphical output of variations in the blood temperature Tb with a curve (FIG. 4). Whereas the switches 52 and 53 are used only when the initial cardiac output COo is measured ("single measurement"), as stated above, the following switches are used mainly when the cardiac output is measured continuously ("continuous measurement").

Figure 6:
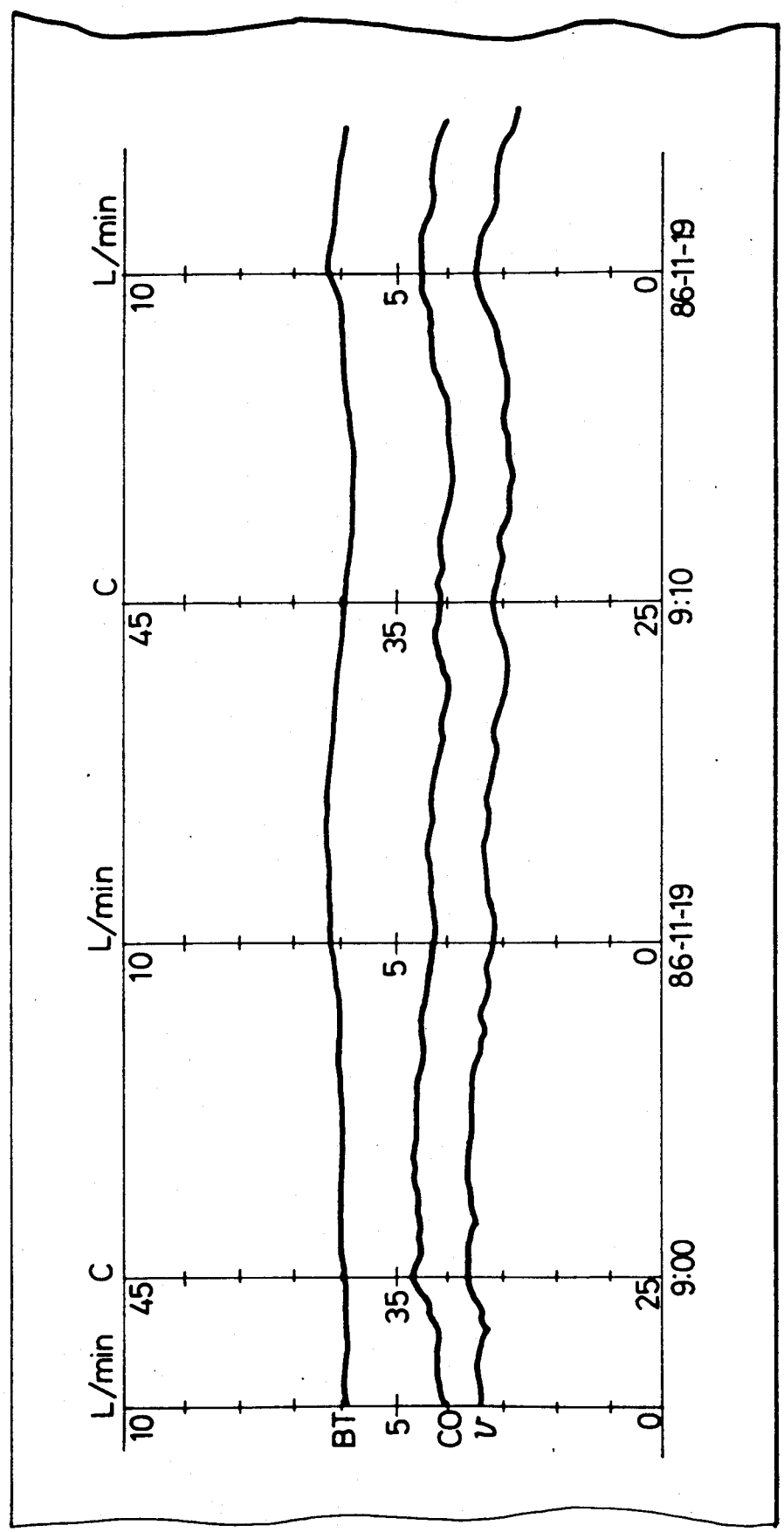
FIGS. 6, 7 and 8 show the examples of the output of the results of continuous measurement.
Figure 7:
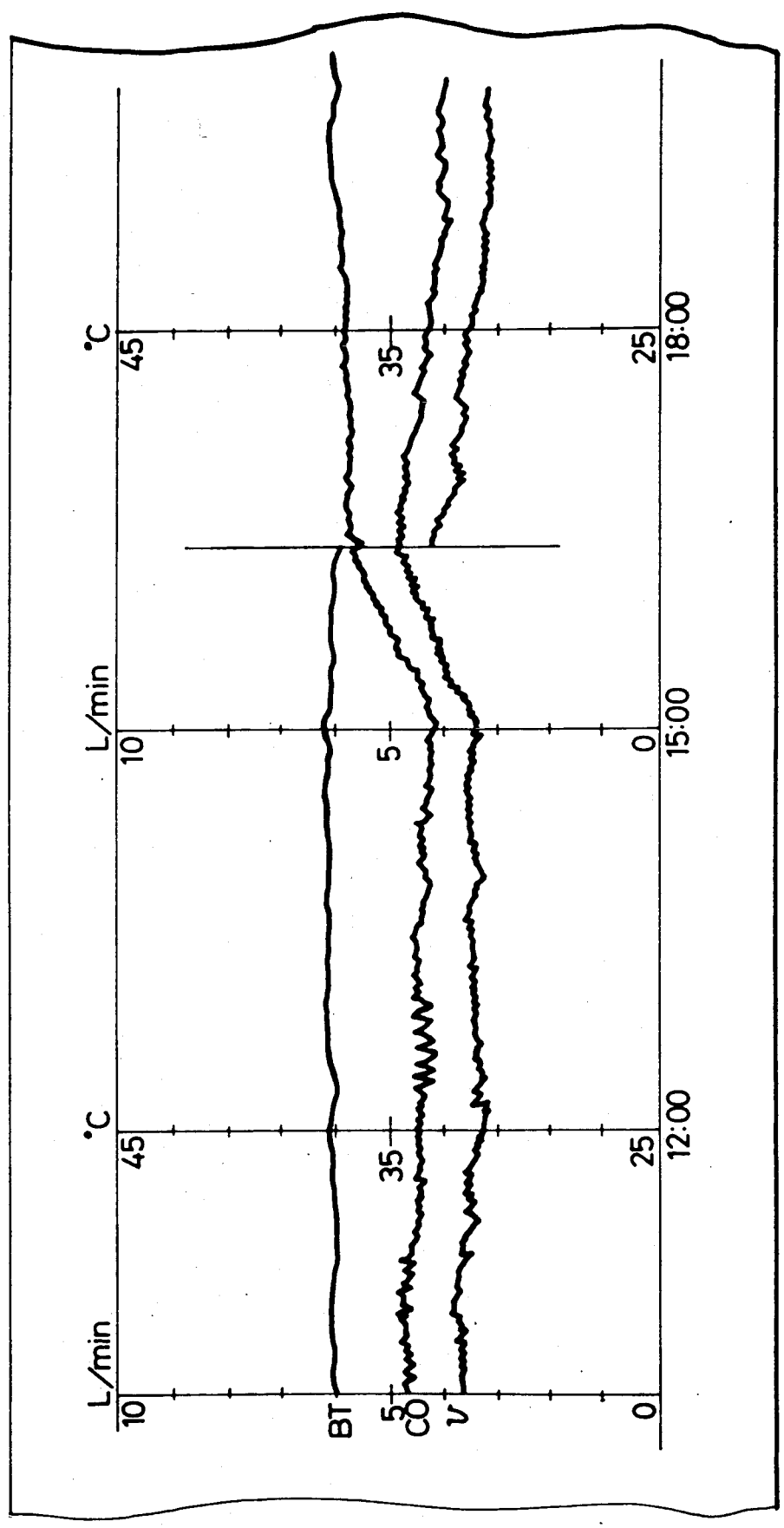
Figure 8:
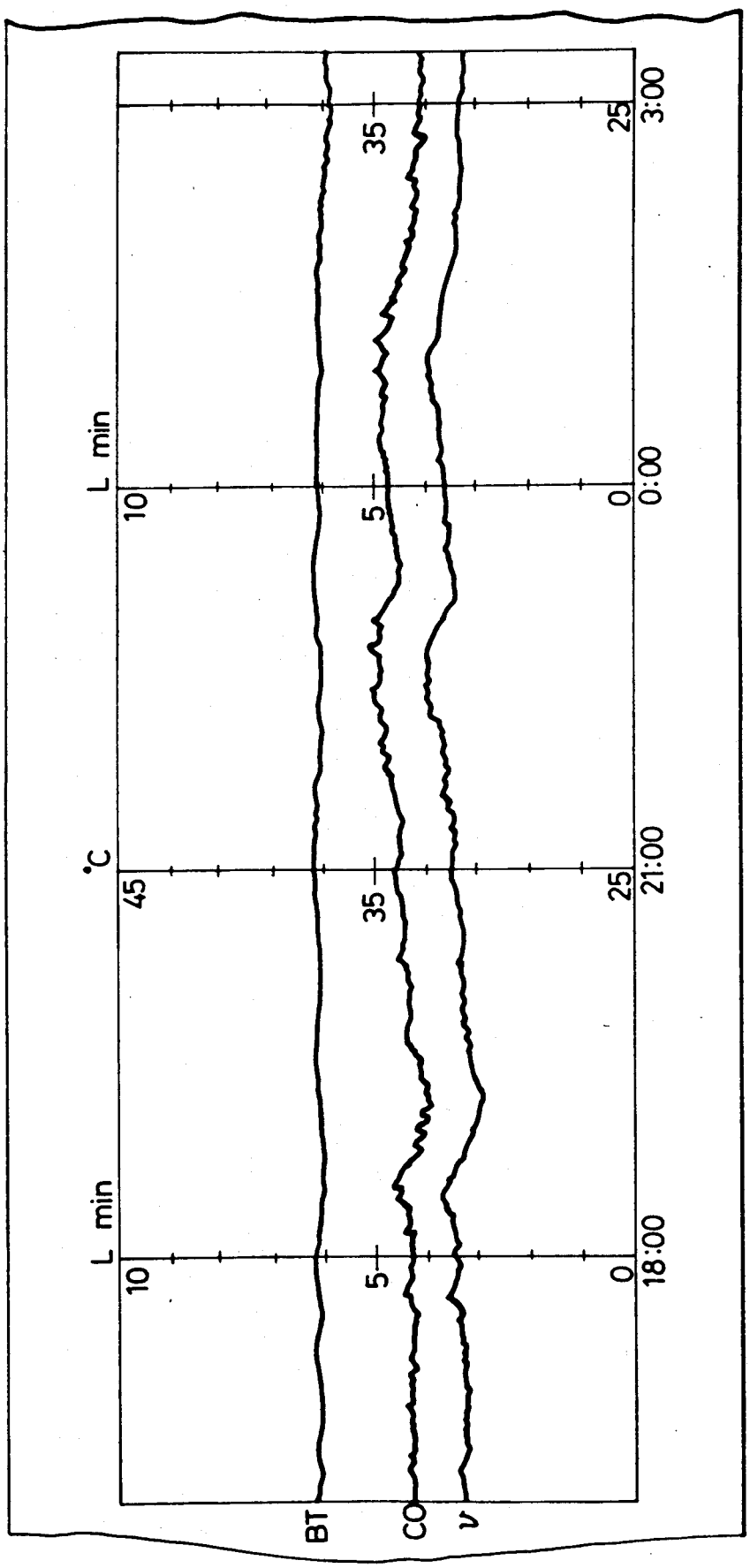

Switches 57 and 58 are used to designate the paper feed speed (which may be 20 mm/hour and 10 mm/min) of the plotter 50. A switch 54 marked "Record" is pressed to output the changes in the cardiac output COx or the like over 12 hours on the plotter 50 (as shown in FIG. 8). A switch 55 marked "Reproduction" is used to output the data which is stored in a memory over 30 minutes, such as the continuously obtained cardiac output COx or the like, on the plotter 50 (as shown in FIGS. 6 and 7). A switch 80 marked "Memo" is a memo switch. By pressing this switch 80, a sheet of recording paper is fed by 6 cm. A switch 56 marked "Continuous Recording" is used to output variations in COi, Tb, Vx or the like on real-time on the recording paper (as shown in FIGS. 6 and 7). In the above-described reproduction mode in which the data stored in the memory over 30 minutes is recorded, the measuring apparatus 100 also measures data such as the cardiac output or the like on real-time and stores the obtained data in the memory. In consequence, the data recorded on the recording paper gradually comes close to and finally coincides with that which is being stored presently. In that case, "reproduction" mode is not stopped but the operation mode is automatically switched over to the above-described "continuous recording".

Switches 59, 60 (FIG. 1A) 61 and 62 (FIG. 1B) are respectively used to manually set the diameter of a catheter (unit: Fr), the volume of injectate (unit: ml), the body surface area of an examinee (unit: m²) and the initial CAL value (unit: L/min) in the apparatus 100. The initial CAL value will be described later in detail. When a figure to be set in each □ in the switches 59 and 62 is larger than that displayed, ▲ is pressed. On the other hand, a smaller figure is set by pressing ▼.

A switch 64, which is indicated as "CONTINUOUS", is used to switch over the operation mode of the apparatus 100 to the continuous mode. The switch 64 lights up when the operation mode is switched over to the continuous mode. A switch 65 indicated as "SINGLE" is a switch/indicator of the single mode, which is pressed when the operation mode is to be switched over from the continuous mode to the single mode to reset the parameter S. The switch 65 lights up when the operation mode is switched over to the single mode. A display 68 is a 4-digit LED which digitally displays the cardiac output. Switches 66 and 67, which are respectively indicated as "BLOOD" and "INJECTATE", are used to designate the type of temperature displayed by a 3-digit LED 69 from among the blood temperature Tb and the injectate temperature Ti.

A switch/indicator 70, which is indicated as "ENTRY", displays that the measuring apparatus 100 has completed the measurement of the initial cardiac output COo by the thermal dilution method and that it is ready to register (enter) the obtained initial cardiac output COo. The initial cardiac output COo is registered by pressing the switch 70 while it is lighting up. Registration of COo is performed for the purpose of obtaining the parameter S. A plurality of initial cardiac outputs COo may be registered in order to increase the accuracy with which the initial cardiac output COo is obtained. More specifically, measurement of the initial cardiac output COo by the thermal dilution method is performed a plurality of times, and the operator selects the reliable data among the obtained data and registers them. The initial value COo is an average value of the registered data.

Lighting up of a switch/indicator 72 marked "START" indicates that preparation of measurement of the initial cardiac output COo by the thermal dilution method is completed. Integration on the basis of the Stewart/Hamilton Equation starts when the switch 72 is pressed while it is lighting up.

A display 71, which is in the form of a bar graph, displays the blood temperature Tb on real-time. Connectors 73 and 74 are respectively connected to a connector 15 of the catheter (FIG. 2A) with the blood temperature sensor incorporated therein and to a connector 16 of a temperature probe 12 (FIG. 2A) for measuring the temperature of an indicator. Reference numerals 63 and 78 respectively denote a power switch and an indicator lamp which indicates the use of a battery incorporated in the apparatus.

A switch 75 shown in FIG. 1C is used to manually set the temperature of an indicator. A reference numeral 76 denotes a connector of an RS232C interface through which the apparatus performs communications with another measuring apparatuses, reference numerals 78 designate terminals for outputting analog signals representing the blood temperature Tb, the blood flow velocity Vx, the cardiac output COx to another measuring apparatuses, and a reference numeral 77 denotes a connector for connecting a power cable.

Function of the Measuring Apparatus 100

The measuring apparatus 100 shown in FIGS. 1A to 1C and 2A to 2C is characterized in that:

(1): In order to eliminate the effect of the indicator remaining in the catheter, a correction table is prepared beforehand. When the indicator is injected so as to allow the initial value COo to be measured by the thermal dilution method, the operator accesses the correction table using the preparatory data representing the outer diameter of the catheter (unit: Fr) and the volume of injectate (unit: ml) which are respectively input by using the switches 59 and 60, in place of inputting the values in the table which are determined on the basis of the results of the experiments beforehand. The effect of the indicator remaining in the catheter also depends on the temperature Ti of the indicator. In this embodiment, the temperature Ti is prepared either by actually measuring it by means of a thermistor 12a of the temperature measuring probe 12 (FIG. 2A) in the manner to be described later or by inputting it by means of the manual switch 69 (FIG. 1B).

(2): Variations in the blood temperature Tb which occurs after the indicator has been injected into the blood are automatically recognized. More specifically, recognition of the starting point of the integration (the point at which the blood temperature Tb changes), which is necessary to accurately perform the integration on the basis of the Stewart/Hamilton Equation (1), can be performed without requiring an operator.

(3): The injectate temperature is measured by using the temperature probe 12. When the probe 12 is not connected to the connector 16 of the measuring apparatus 100, this non-connection is detected, and the value set beforehand in the switch 75 (FIG. 1C) provided on the rear surface of the apparatus is therefore used as the injectate temperature Ti.

(4): Once the initial cardiac output COo has been measured by the thermal dilution method and the parameter s has been obtained from the initial cardiac output, the cardiac output COi, the blood temperature Tb, the blood flow velocity Vx and so on are continuously stored in the memory. The data stored in the memory are output on the recording paper in any of the following forms, when necessary:

(i) The COx or the like which is being measured is output on the recording paper in the plotter 50 substantially on real-time (as shown in FIGS. 6 and 7). This is accomplished by pressing "CONTINUOUS RECORDING" switch 56.

(ii) The data stored in the memory over 30 minutes, which represents COx and so on, is reproduced (as shown in FIGS. 6 and 7) by pressing "REPRODUCTION" switch 55. As stated above, the "REPRODUCTION" mode is automatically switched over to the "CONTINUOUS RECORDING" mode.

(iii) The data representing COx and so on which have been obtained over 12 hours is reproduced on the plotter 50 in a compressed fashion (as shown in FIG. 8). This is accomplished by pressing "RECORD" switch 54. In the case of a patient who is required to lie quietly in a quiet place, the data collected is stored in the memory in place of being recorded by the plotter 50. The data stored can be output later whenever necessary by pressing the switch 54.

(5): The parameter s can be manually set by means of the switch 62 so as to enable COx to be continuously obtained from the parameter s set in this manner and the blood flow velocity Vx. This is helpful to obtaining relative changes in COx.

(6): Changes in the blood temperature Tb which occur when the initial cardiac output COo is obtained by the thermal dilution method can be visually confirmed by means of the bar graph display 71. The bar graph display is capable of fixedly displaying the base line (reference temperature Tbo) and the maximum temperature Tbmax of the blood temperature, in addition to the changes in the temperature with time.

(7): The data stored in the memory is protected from the power failure or the like by means of the battery (denoted by a reference numeral 148 in FIG. 9). Voltage drop in the battery 148 is informed by the lighting up of the LED 78.

(9): Analog signals representing the cardiac output and so on can be output by means of an analog output circuit (denoted by reference numerals 142 and 151) from the terminals 78 to an external measuring apparatus other than the measuring apparatus 100.

(10): Digital signals representing COx and so on can be output by means of a circuit (designated by a reference numeral 144 in FIG. 9) from the RS232 interface to an external measuring apparatus.

Structure of Catheter

FIG. 2A shows a catheter which incorporates a thermistor for measuring the blood temperature Tb in accordance with the thermal dilution method and a thermistor for measuring the blood flow velocity V. In FIG. 2A, a catheter 4 is constructed so that it has four lumens. The catheter 4 has a pressure detection port 18 formed at the forward end thereof. A balloon 17 with a flexible elastic body is mounted on the catheter tube at a position a few millimeters away from the forward end thereof in such a manner that it encloses the entire forward end of the catheter tube. The catheter has a hole 25 formed in the portion of the catheter tube which is covered by the balloon. Air (preferably, carbon dioxide) is injected into or drawn from the balloon 17 through this hole 25 so as to inflate or deflate the balloon 17. A thermistor 1 is provided on the catheter tube at a position which is 10 to 20 mm away from the forward end, and a thermistor 2 is disposed at a position which is 10 to 15 mm closer to the proximal end of the catheter from the position of the thermistor 1. The catheter 4 also has a injection port 3 at a position which is separated from the thermistors 1 and 2 by 8.5 to 38 cm and which is separated from the forward end by 12 to 40 cm. The thermistor 1 is used to measure the heat balanced temperature which is required to measure the blood flow velocity Vo (or Vx), and the thermistor 2 is employed to measure the temperature Tb of the blood diluted, which is required to measure the initial cardiac output COo by the thermal dilution method. The injection port 3 is a port through which the indicator is discharged into the blood.

The catheter 4 shown in FIG. 2A is introduced from the cervical vein, the femoral vein or the basilic vein. At that time, the forward end of the catheter 4 passes through the superior vena cava or the inferior vena cava, the right atrium and then the right ventricle, to rest in the pulmonary artery. In view of the blood flowing from the proximal end of the catheter toward the forward end thereof, the thermistor 2 is located on the side of the injection port 3 which is closer to the forward end (which is downstream of the injection port 3). On the other hand, in the case of a catheter of the type which is introduced from the peripheral artery and is employed in the aorta, the blood flows in the reverse direction relative to the catheter, and the thermistor 2 is therefore disposed on the side of the injection port 3 which is closer to the proximal end of the catheter.

FIG. 2B is a cross-section of the essential parts of the catheter 4. As shown in FIG. 2B, the pressure detection port 18, the balloon side hole 25 (which is shown in FIG. 2A), the thermistors 1 and 2, and the injection port 3 respectively communicate with the four lumens, which are a pulmonary arterial pressure lumen 19, a balloon lumen 20 which serves as a passageway for the air with which the balloon 17 is inflated or deflated, a thermistor lumen 21 for accommodating the thermistors 1 and 2 and the leads thereof, and an injection lumen 23 through which the dilution indicator passes. These four lumens are provided independently of each other, and are respectively further connected at the rear end portion of the catheter to a pulmonary arterial pressure measuring tube 8, a balloon tube 6, a thermistor tube 13 and an indicator injection tube 10, as shown in FIG. 2A. The rear ends of the tubes 8, 6 and 10 are respectively provided with connectors 7, 8 and 11. The thermistor tube 13, through which leads 22 and 24 of the thermistors 1 and 2 pass, is connected to the connector, which is in turn connected to the connector 73 of the measuring apparatus 100.

The catheter shown in FIGS. 2A to 2C will be described in detail below. FIG. 2B is an enlarged cross-section of the portion of the catheter on which the thermistors 1 and 2 and the balloon 17 are mounted, and FIG. 2C is a section taken along the line III—III' of FIG. 2B. As shown in FIG. 2C, the catheter 4 has four lumens which are the balloon lumen 20, the pulmonary arterial pressure lumen 19, the injection lumen 23 (FIG. 2C), and the thermistor lumen 21. The balloon lumen 20, which has the balloon side hole 25, communicates with the balloon tube 6. The pulmonary arterial pressure lumen 19 with the pressure detection port 18 communicates with the pulmonary arterial pressure measuring tube 8. The injection lumen 23 has the injection port 3 at a position which is separated from the forward end of the catheter by 12 to 40 cm. The injection lumen 23 communicates with the indicator injection tube 10 provided at the proximal end of the catheter. The thermistor lumen 21 has side holes 26 and 27 on which the thermistors 1 and 2 are mounted at a position which is separated from the forward end of the catheter by 1 to 2 cm and at a position which is separated from the position of the side hole 26 by 1 to 1.5 cm toward the proximal end of the catheter, respectively. The leads 22 and 24 for the thermistors 1 and 2 are passed through the lumen 21. The proximal end of the lumen 21 communicates with the thermistor tube 13.

It is preferable for the thermistor 1, which may be of the self-heating type, to be located downstream of the thermistor 2. More specifically, when the cardiac output is to be measured by means of the catheter 4, it is necessary that the temperature of the diluted blood be measured by the thermistor 2 with a high degree of accuracy. If the thermistor 1 is located downstream of the thermistor 2, the thermistor 2 will be less affected by the self-heating type thermistor 1. Despite of this, the thermistor 1 may be provided in a different position from that shown in FIG. 2A, i.e., it may be located upstream of the thermistor 2 by 10 to 15 mm so that it can be correctly located within the pulmonary artery.

The thermistor 1 employed in the catheter 4 is characterized in that $B_{25-45}=3500K$, in that $R(37)=1000\,\Omega$, and in that it has dimensions of $1.18^l \times 0.4^w \times 0.15^t$ (unit: mm). The thermistor 2 is characterized in that $B_{25-50}=3500K$, in that $R(37)=14\,k\Omega$, and in that it has dimensions of $0.75^l \times 0.1^w \times 0.15^t$ (unit: mm). It is preferable for the thermistor 1 to be of the type which has a calorific value ranging from 0.01 joules to 50 joules. If the thermistor 1 has a calorific value higher than this value, the blood temperature may rise, or the wall of the blood vessel may be damaged when the thermistor 1 makes contact with it. With the thermistor 1 having a calorific value lower than the above-described value, the detection sensitivity may be deteriorated. The thermistor 2 may also be characterized in that $B_{25-45}=3980K$, in that $R(37)=40\,k\Omega$, and in that it has dimensions of $0.50^l \times 0.16^w \times 0.15^t$ (unit: mm).

The injectate temperature measuring probe 12 shown in FIG. 2A has a thermistor 12a in the vicinity of the forward end thereof. The rear end of the probe 12 is connected to a connector 16, which is in turn connected to the connector 74 of the measuring apparatus 100.

Operation Procedure of the Measuring Apparatus

The operation procedure of the measuring apparatus 100 will be described in detail below with reference to FIGS. 1A, 1B, 3A and 3B.

First, in step S1, the injectate temperature probe 12 is connected to the measuring apparatus 100. Next, in step S2, the probe 12 is immersed in the indicator contained in an ice-cooled container (which is provided within the measuring apparatus 100). The indicator may be a physiological salt solution or the like. Thereafter, the catheter 4 is primed in step S3, and it is then inserted into the pulmonary artery in step S4. The catheter 4 is introduced from the vein or the like of the superior limb or the inferior limb, and is finally led into the pulmonary artery. In step S5, the connectors of the catheter shown in FIG. 2A are connected to the measuring apparatus body 100. Once the connectors have been connected to the apparatus, the position of the catheter 4 which is moving within the blood vessel is detected on the basis of the blood pressure, such as the central venous pressure, the right atrium pressure, the right ventricle pressure or the pulmonary arterial pressure, as well as the pressure waveforms, the blood pressure being detected through the pressure detection port 18, the tube 8 and the connector 9. After the catheter reaches its predetermined final position, the pulmonary arterial pressure is measured, and then the pulmonary artery wedge pressure is obtained by closing the pulmonary artery by means of the inflated balloon 17.

Next, in step S6, certain values are set in the switches 59, 60 and 61. The switch 62 is used when a relative COx is to be measured (which will be described later). The switch 62 is not thus used when the initial cardiac output COo is to be measured by the thermal dilution method.

In step S7, the measuring apparatus is turned on. In step S8, it is determined whether or not there is an abnormal display (which indicates the failure of the apparatus), and then the lighting up of the SINGLE indicator 65 is awaited in step S9. Once the indicator 65 lights up, the BLOOD indicator 66 lights up, which indicates that the temperature displayed on the display 69 is the blood temperature Tb. If it is desired to display the injectate temperature at that time, the display of the display is switched over to that of the injectate temperature Ti by pressing the INJECTATE switch 67. At that time, the bar graph display 71 is displaying the base line of the blood temperature Tb.

The display of Ti is automatically switched over to that of the blood temperature Tb after 30 seconds have elapsed, and Tb is thereby displayed again on the display 69. This arrangement is made because the display of Tb is more significant to the operator than that of Ti.

Thereafter, in step S10, the lighting up of the START indicator 72 is awaited. The lighting up of the START indicator 72 means that preparation for measurement of the initial cardiac output COo by the thermal dilution method has been made. Next, in step S11, either the switch 52 or the switch 53 is pressed, if necessary, to select the form in which the data is output to the plotter 50. In step S12, a cock 11 is opened to inject the indicator into the blood vessel.

After the injection, the measuring apparatus 100 automatically reads the changes in Tb and determines the optimal point at which integration is started. If the operator presses the START switch 72 before the optimal point is detected, integration of Tb is started at that point. If the switch 72 is not pressed, the apparatus determines the optimal point at which integration of Tb is started by itself. It generally takes somewhat more than 10 seconds for the calculation of the cardiac output by the thermal dilution method to be completed. The changes in Tb which occur during the calculation are stored in a predetermined memory (which is a RAM 132 shown in FIG. 9). At the same time, they are displayed by the display 69 and the bar graph display 71. Furthermore, changes in the blood temperature Tb are output to the plotter 50, as shown in FIG. 4, if the switch 53 has been pressed beforehand. The operator can confirm the normal operation of the apparatus with these displays. In the graph shown in FIG. 4, the axis of the ordinate rises as the blood temperature Tb falls. The date, the time and so on of the measurement may also be output on the graph for the convenience of the examiner. The graph shown in FIG. 4 may be output at a speed of 300 mm/min.

Once the cardiac output COo has been measured by the thermal dilution method, the obtained value is digitally displayed by the display 68. Concurrently with this, the results of the measurement shown in FIG. 5 are output by the plotter 50, if the switch 52 has been pressed. The table shown in FIG. 5 lists the date and the time of the measurement, the cardiac output CO, the body surface area BAS which is input by means of the switch 61, the blood temperature BT(=Tb), the catheter outer diameter CAT(=Fr), the injectate volume IV(Vi), the cardiac coefficient CI (=CO/BSA), the injectate temperature IT(=Ti), and an indication of "ENTRY" which indicates that that cardiac output has been registered. Completion of the measurement of the initial cardiac output COo can be confirmed by the lighting up (in step S15) of the ENTRY indicator 70.

If the operator judges that the data thus-obtained is reliable, he or she presses the ENTRY switch 70 (in step S17) to register the data. After a while, the START indicator 72 lights up again, and the measurement of the initial cardiac output COo by the thermal dilution method is thereby completed.

When a more accurate CO is desired, a plurality of data are registered by pressing the ENTRY switch 70 each time data is obtained by repeating the processings from step S11 to step S17. An average value of the plurality of COo values is then obtained to determine the initial cardiac output COo.

Once the sufficiently reliable initial cardiac output COo has been obtained, continuous measurement of COx is started. This is performed only by pressing the CONTINUOUS switch 64. When the switch 64 is pressed, the CONTINUOUS indicator 64 lights up, and the operation mode of the measuring apparatus is switched over to the continuous measurement mode. The operation mode can be reset to the single mode by pressing the SINGLE switch 65.

In the continuous measuring mode, if the continuous recording switch 56 has been pressed, the blood temperature $BT(=Tb)$, $CO(=COx)$, and the blood flow velocity $(=Vx)$ are output on the plotter 50, as shown in FIGS. 6 and 7. FIG. 6 shows an example of the graph which is output at a paper feeding speed of 10 mm/min, and FIG. 7 shows an example of the graph which is output at a speed of 20 mm/hour. Although not shown in FIGS. 6 and 7, various types of data, such as those shown in FIG. 5, may also be output together with the graph. In the example shown in FIG. 7, the measurement of the initial cardiac output COo was performed the second time at about 16:30. As shown in FIG. 7, a vertical line is used to indicate the fact that measurement of the initial cardiac output COo is performed in the measuring apparatus 100.

Structure of the Measuring Apparatus

Figure 9A:
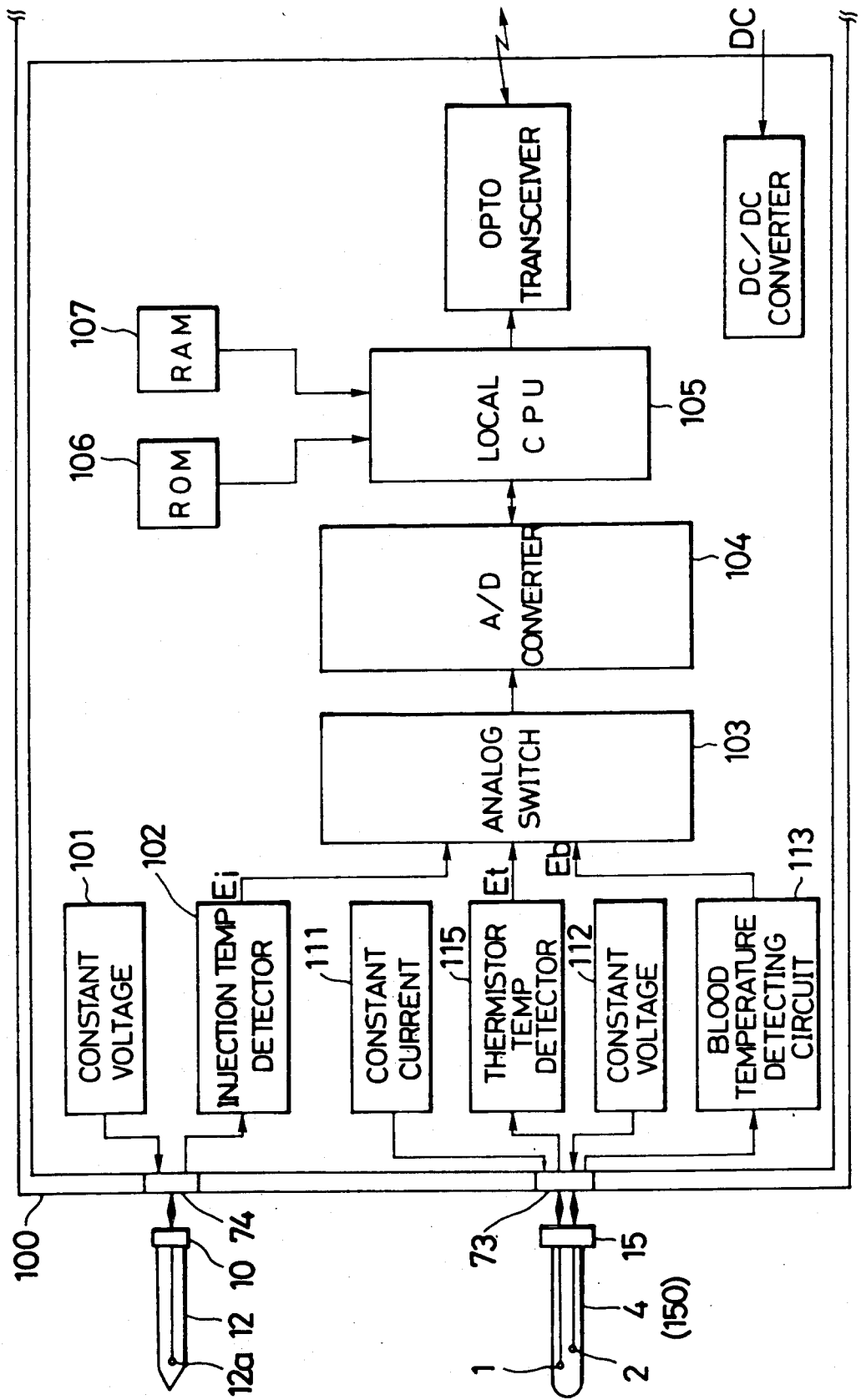
FIGS. 9A and 9B are circuit diagrams of the major portions of the measuring apparatus of FIG. 1.
Figure 9B:
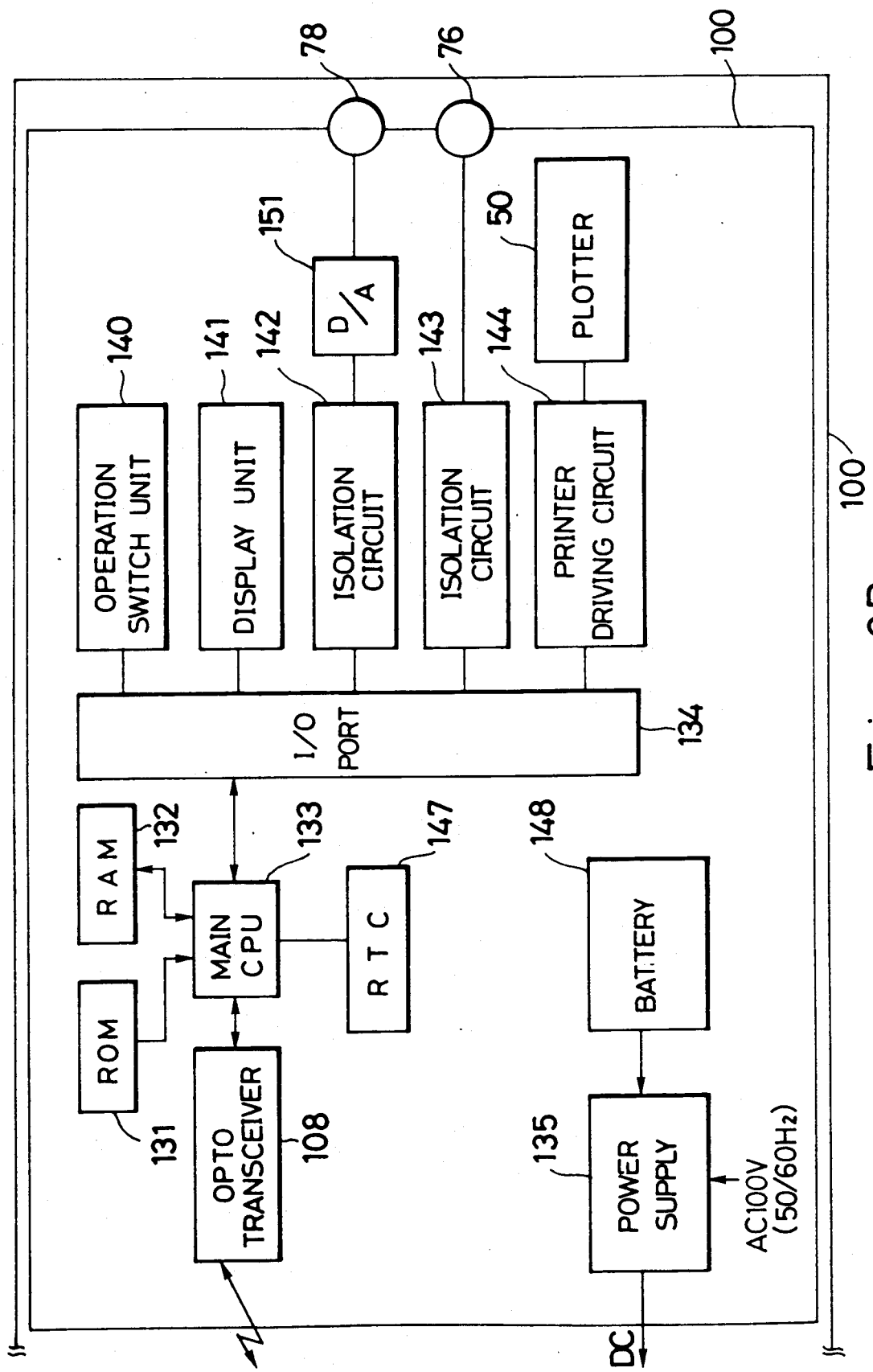

FIG. 9 is a circuit diagram of the measuring apparatus 100 with the catheter 4 and the injectate temperature probe 12 being connected thereto. The measuring apparatus 100 includes two measuring circuits 120 (FIG. 9A) and 130 (FIG. 9B), which are electrically isolated from each other. The measuring circuit 120 has the function of converting the electrical signals from the thermistors 1 and 2 incorporated in the catheter 4 and the thermistor 12a in the probe 12 into temperature data and of sending it to the measuring/recording circuit 130 through an optical communication circuit 108. The measuring/recording circuit 130 has the function of operating from the temperature data from the measuring circuit 120 the initial cardiac output COo, the blood flow velocity Vo (or Vx), the parameter S, the continuous cardiac output COx and so on and of displaying the data on the plotter 50 or other various types of displays. The measuring circuit 120 is controlled by a local CPU 105, and the measuring/recording circuit 130 is controlled by a main CPU 133.

Measuring Circuit 120

A catheter type sensor 150 shown in FIG. 9 employs the catheter shown in FIG. 2A. The sensor 150 incorporates the self-heating type thermistor 1 for detecting a heat-balanced temperature, and the thermistor 2 for detecting the temperature of the blood in the pulmonary artery. The catheter type sensor 150 is introduced into the pulmonary artery by the right heart catheterization in the manner described above. The connector 15 of the sensor 150 is connected to the connector 73 of the apparatus body 100. The thermistor 2 is connected through the lead 24 to a constant-voltage circuit 112 for driving the thermistor 2 and to a blood temperature detecting circuit 113 for detecting the temperature of the blood.

The pulmonary artery blood temperature from the thermistor 2 is detected by the blood temperature detecting circuit 113 as a voltage signal Eb. The thermistor 1 is connected through the lead 22 to a thermistor temperature detecting circuit 115 and to a constant-current circuit 111. The constant-current circuit 111 supplies a predetermined amount of current Ic to the thermistor 1 to heat it. The temperature signal detected by the thermistor 1 is sent to the thermistor temperature detecting circuit 115 where it is detected as a voltage Et. The thermistor 12a incorporated in the injectate temperature probe 12 is driven by a constant-voltage circuit 101, and the changes in the temperature detected by the thermistor 12a are detected by a injectate temperature detecting circuit 102 as a voltage Ei. The local CPU 105 receives these three voltages Ei, Et, and Eb, and converts them into the injectate temperature Ti, the resistance Rt of the thermistor 1, the temperature Tt of the thermistor 1, and the blood temperature Tb.

The operation of the local CPU 105 will be further described in detail below. The local CPU 105 inputs Ei, Et and Eb to a 14-bit A/D converter 104 on the time-sharing basis by driving an analog switch 103 having the multiplex function, and then stores the resultant digital values sequentially in a RAM 107. The digital values are converted into temperature data using the voltage-temperature conversion table stored in a ROM 106. The resistance Rt of the thermistor is obtained by the following equation.

$$Rt = Et/Ic$$

where Ic is the current that flows in the thermistor. The local CPU 105 sends the data, such as Ti, Rt, Tt, and Tb, to the measuring/recording circuit 130 through an optical communication line. The communication control (which may be performed by the known polling-/selecting method) is performed by the local CPU 105 and the main CPU 133.

The use of the 14-bit A/D converter 104 having a relatively high resolution enables the measurement of a high cardiac output area which will be described later.

Measuring/Recording Circuit 130

The measuring/recording circuit 130 receives by using the above-described simple communication control procedure the injectate temperature Ti, the resistance Rt of the thermistor 1, the temperature Tt of the thermistor 1, the blood temperature Tb and so on and stores the data ordered in time in a RAM 132. The CPU 133 then operates the initial cardiac output COo, the blood flow velocity Vo (or Vx), the continuous cardiac output COx from the data that it received.

An RTC (real time clock circuit) 147 counts the real time. Also, it monitors the time, e.g., 30 seconds in which the display of Ti is to be changed to that of Tb in the LED display 69.

FIG. 10A shows the structure of the data stored in the RAM 132. The capacity of the RAM 132 is divided into an area (132a) in which data such as Tb obtained by A/D converting the data each 40 ms over 30 minutes is stored, an area (132b) in which the data such as the continuous cardiac output COx which is obtained over 30 minutes at an arbitrary time is stored, and an area (132c) in which average values of data such as continuous cardiac output COx obtained over 12 hours in 1.5 minutes are stored.

FIG. 10B shows how three address counters 160, 161 and 162 for storing data in the RAM 132 correspond to the three areas (132a, 132b, 132c). The data storage address counter (an SC pointer) 160 is used to point the address at which the data from the measuring circuit 120 is stored in the RAM 132. The data read-out address counter (an RC pointer) 161 is used to point the address of the data to be read out from the RAM 132 when the initial cardiac output COo is calculated or the address at which the calculated value is stored in the RAM. The data print address counter (a PC pointer) 162 points the address of the data to be output to the plotter 50. This embodiment employs three pointers, because the data storage, the data read-out and the data output are performed independently of each other.

Calculation of Initial Cardiac Output COo

Figure 11:
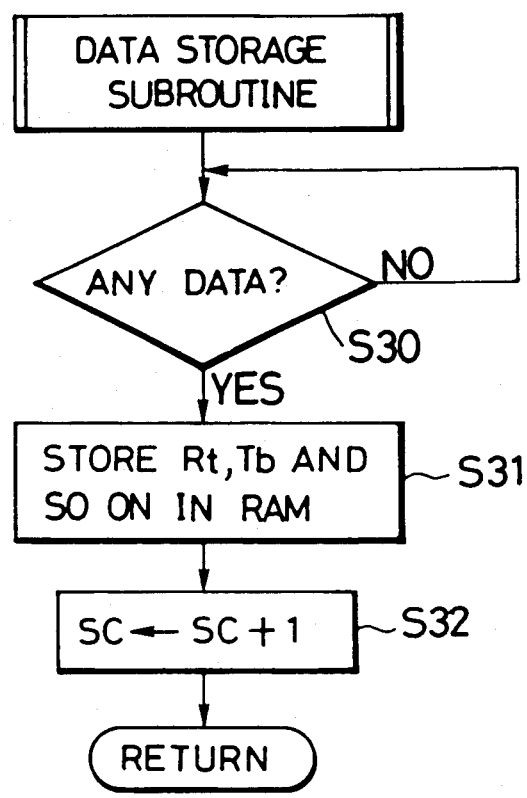

FIG. 11 is a flowchart of the subroutine executed by the main CPU 133 when it receives the data from the local CPU 105 and stores them in the RAM 132. As stated above, the SC pointer is used when data is stored in the RAM 132.

Figure 13A:
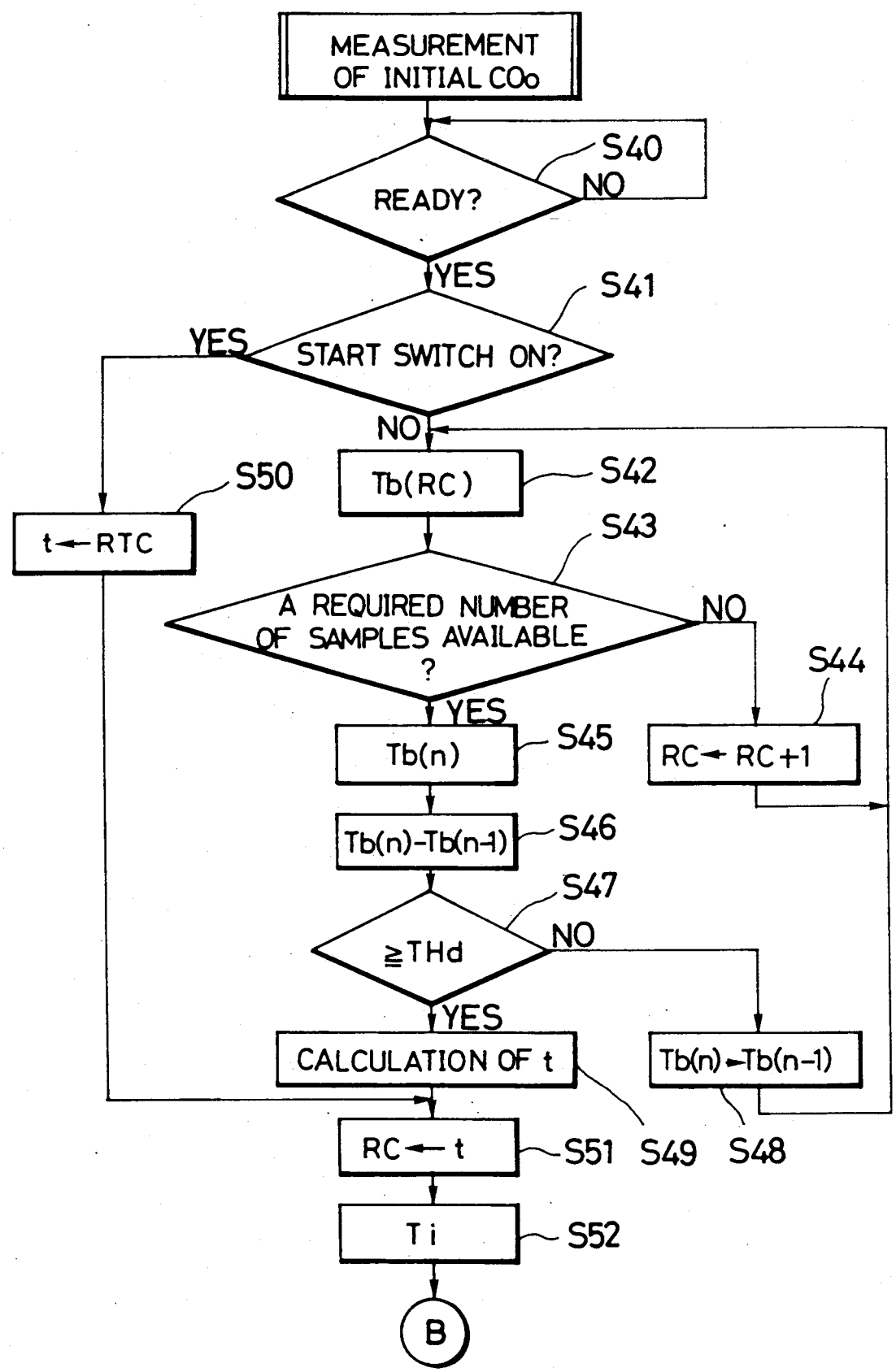

FIGS. 13A and 13B are flowcharts of the control routine which is executed by the CPU 133 when it calculates the initial cardiac output COo. The control routine shown in FIGS. 13A and 13B includes the automatic measurement starting function.

Manual Start

First, in step S40, it is determined whether or not the measuring apparatus is in a ready state. It is determined that the apparatus is ready when the blood temperature Tb is detected under the stable condition with no failure in the hardware of the apparatus. In order to determine that Tb is in a stable state, variance of Tb in a fixed period of time is operated, and as to whether the variance is equal to or smaller than a predetermined value is then determined. Once it is detected that the apparatus is in a ready state, the START indicator 72 lights up, as stated above. It is then determined in step S41 whether or not the START indicator 72 has been pressed.

Figure 17:
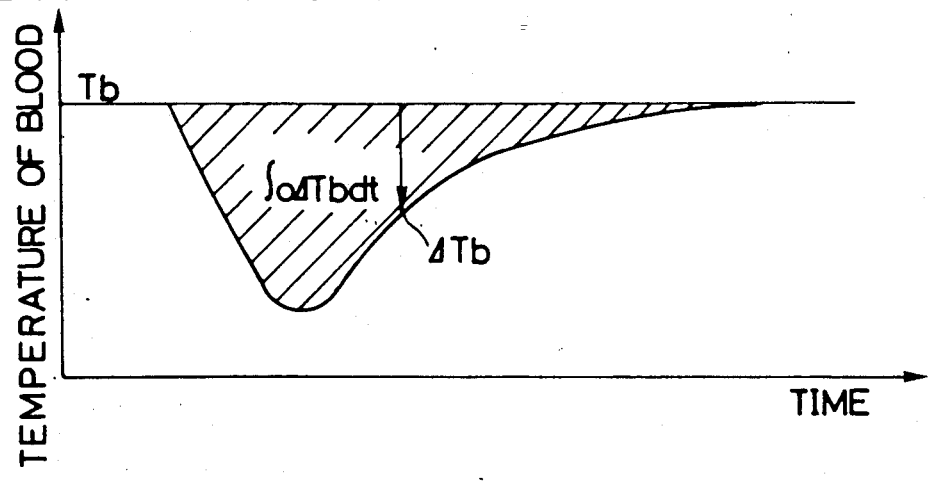

If the START indicator 72 has been pressed, it is determined that an instruction of starting of manual measurement has been given by the operator. In consequence, in step S50, the time t is read by the real time clock RTC 147, and the pointer value corresponding to the time t read is then set in the RC pointer 161 in step S51. Thereafter, in step S52, the injectate temperature Ti is fetched from the RAM 132. In step S53, one Tb designated by the RC pointer 161 is read out from the RAM 132. In step S54, the base line temperature Tbo is detected from the data stored in the memory before the time t. Tbo may be the average temperature of the small variance which is used in the determination of the ready state of the apparatus. Next, in step S55, $\Delta Tb$ (FIG. 17) is calculated using the following equation.

$$\Delta Tb = Tbo - Tb$$

where the sign of the blood temperature Tb is positive in the temperature downward direction. In step S56, $\Sigma \Delta Tb$ (integration) is calculated. $\Sigma \Delta Tb$ corresponds to $$\int_0^\infty \Delta Tb \, dt$$

in the Stewart/Hamilton Equation. Thereafter, it is determined in step S57 whether or not the blood temperature has dropped within a fixed period of time. If it is determined in step S57 that the temperature drop $\Delta Tb$ is smaller than a predetermined threshold THa, i.e., if it is determined that the indicator does not reach the thermistor 2 yet, the counter ERTIM is incremented by one in step S58. If $\Delta Tb$ remains equal to or smaller than THa until the ERTIM overflows, it is determined that the apparatus is in an abnormal state, and an error display is conducted in step S60. In this erroneous state, the display 68 displays "Er", as well as an error code number.

If the apparatus is operating normally and if the indicator is injected, it is determined in step S57 that $\Delta Tb > THa$ within a fixed period of time. In the loop consisting of steps S53, S54, S55, S56, S57, S58 and S59, the integration ($\Sigma \Delta Tb$) is performed in step S56. However, since the difference between the blood temperatures Tb and Tbo is substantially 0, the results of the integration performed in step S56 is 0. Noise may be generated. However, variations caused by the noise have both positive and negative values, so the results of the integration is also 0.

Once it is detected in step S57 that $\Delta Tb > THa$, the process goes to step S61 where the peak of the dilution curve is detected. Tbmax used in step S61 represents the maximum temperature drop from Tbo which occurs while the temperature is lowering. Tbmax is initially set to 0. Once the temperature drops (until the peak is detected), it is determined in step S61 that $$\Delta Tb > \Delta Tbmax,$$

so $\Delta Tbmax$ is updated in step S62. In step S63, temperature $\Delta Tbc$ (used in step S68) which serves as the standard point at which the integration is suspended is updated. Theoretically, the longer the period during which the integration is performed, the higher the accuracy. In the Stewart/Hamilton method, the period of the integration may be hence any value including an infinity. However, the long period of the integration does not ensure high measurement efficiency. Furthermore, in the vicinity of Tbo, the results of the integration is easily affected by noise. So, $\Delta Tbc$ has to be the lower limit value which ensures both the sufficiently high accuracy and the sufficiently high measurement efficiency (the period of the integration is shortened). Since the magnitude of the peak temperature $\Delta Tbmax$ affects the $\Delta Tbc$, $\Delta Tbc$ is updated in step S63 each time $\Delta Tbmax$ is updated. In step S64, the RC pointer is incremented so that it points new temperature data. Thereafter, the process returns to step S53 to repeat the above-described processing. Thus, the integration is continued until the peak of the dilution curve is detected.

Figure 18:
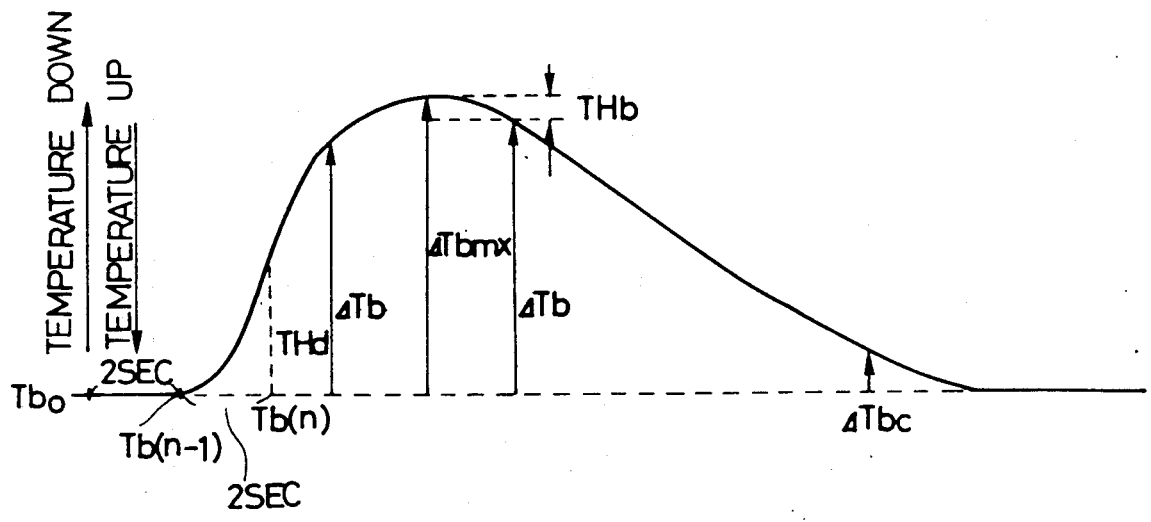
FIG. 18 is a graph, explaining the operation of automatic starting of the cardiac output measurement.

Once the blood temperature drop stops, the answer of the determination made in step S61 becomes negative, and the process goes to step S66 where it is determined whether or not $$\Delta Tbmax - \Delta Tb > THb,$$

where THb is a predetermined threshold. As shown in FIG. 18, when the above-described condition is satisfied, it is considered that the dilution curve has passed its peak, and the peak flag is then set in step S67. The peak flag indicates that the peak has been detected at least once after the measurement had been started.

Thereafter, it is determined in step S68 whether or not the blood temperature has gone up (the dilution curve drops) and reached a critical temperature $\Delta Tbc$ at which integration is to be stopped.

If the temperature rise $\Delta Tb$ does not yet reach $\Delta Tbc$, the process goes to step S64, and then returns to step S53 to continue the integration.

Once the temperature rise $\Delta Tb$ reaches $\Delta Tbc$, the processing proceeds to step S69 where the peak flag is checked. Since the peak flag has been set, the processing proceeds to step S70 and the initial cardiac output COo is operated. This clarifies the significance of the peak flag: it may be possible that it is determined in step S68 that $\Delta Tb \leq \Delta Tbc$ before no peak has been detected. So, only when the peak represented by $\Delta Tbmax - \Delta Tb > THb$ has been detected, the peak flag is set, preventing erroneous stoppage of the integration, which would occur when the peak flag is not set. If THa and THb are the same threshold, the processings related to the setting of the peak flag (in steps S66, S67, S69 and S70) are eliminated.

For the purpose of increasing the accuracy with which the integration is conducted, $\Delta Tbc$ is preferably set to a value which is substantially the same as $\Delta Tbo$. The processings in step S70 to S75 will be described later after automatic starting of the measurement has been described.

The operation of the initial cardiac output COo is thus performed when measurement is manually started.

Automatic Starting

Next, the case in which it is determined in step S41 that the START switch 72 has not been pressed will be described below. Non-pressing of the START switch 72 is detected either when the operator intends to automatically start the measurement or when the operator does not yet press the START switch 72. Furthermore, in this embodiment, it is determined that the operator intends to start the measurement automatically when there exists predetermined changes in the temperature Tb. In other words, while the START switch 72 is not being pressed, both the changes in the temperature Tb and the pressing of the switch 72 have to be monitored. This monitoring of the temperature is performed in step S43 and the subsequent steps. Pressing of the switch 72 is detected as an interrupt in the loop consisting of steps S42 to S47. Once the interrupt occurs in the above-described loop, the processing forcibly goes to step S50.

If it is detected that the switch 72 has not been pressed, Tb is read out of the RAM 132 in accordance with the RC pointer 161 in step S42. In this embodiment, since a change in Tb is represented by a moving average value (of 16 samples) of Tb, a required number of samples are fetched from the memory 132 in the loop consisting of steps S42, S43, and S44. The moving average value is one sample data. Once the required number of samples have been obtained, a total number of samples required to obtain the average value are obtained each time one sample data is read out from the memory 132. In step S45, the moving average value, Tb(n), is obtained. In step S46, the difference between this moving average value and the preceding moving average value Tb(n−1) is obtained. If the difference is equal to or larger than a predetermined threshold THd, it is determined that the temperature of the blood has changed due to the injectate, and the time t at which this change takes place is then calculated in step S49. Calculation of the time t is necessary, because the detection of the change in the temperature is delayed from the time at which change in the temperature actually occurs. The subsequent processings are the same as those executed when pressing of the START switch 72 is detected.

If it is determined in step S47 that the change in the temperature is smaller than the threshold THd, the present average value Tb(n) is moved into the preceding average value Tb(n−1) storage area in step S48.

Next, the relationships between the moving average interval (which is 640 ms = 40 ms × 16, in the above-described example), the time difference between Tb(n) and Tb(n−1), and the threshold THd will be described. In the control processing shown in FIG. 13A, it is detected that there is a change in the dilution curve of the cardiac output when the change in the temperature (= temperature gradient) with time, which is expressed by:

$$\frac{Tb(n) - Tb(n-1)}{\text{Difference between } n \text{ and } n - 1}$$

exceeds THd. The difference between n and n−1 is 640 ms. It is preferable for THd to be set at about 0.1° C. from the viewpoint of detection of changes in the dilution curve without being affected by noise or the like. In the case of the dilution curve of a human being, it takes about 2 seconds for the change of 0.1° C. to appear in the curve. Hence, it is necessary for the control processing shown in FIG. 13A to be slightly altered as follows: The moving average operation of the dilution curve temperature Tb is performed at each 16 samples (= 640 ms), and the results of the operation are stored in the memory. The difference between the present moving average value, which is represented by Tb(k), and the moving average value Tb(l), which has been obtained and stored about 2 seconds before, is divided by 2 to obtain the curve gradient, and this gradient is then compared with THd = 0.1° C. More specifically, if $$\frac{Tb(k) - Tb(l)}{2 \text{ seconds}} \geq 0.1,$$

it is determined that the change in the temperature caused by the heart beat has occurred. In the case where the curve gradient is found from the data previously obtained 2 seconds before to determine the integration interval, t, which is operated in step S49 in FIG. 13A, means the data which has been obtained 2 seconds before.

In order not to synchronize the moving average operation cycle with the time interval of 2 seconds, all of the individual Tb(k) have to be stored in the above-described example. So, the average value Tb(l) may be replaced by the real time value Tb obtained 2 seconds before.

Integration calculation is thus performed when it is manually or automatically started.

Tabulation of Correction Factor

The processing executed in step S71 will be described below. As stated above, Stewart/Hamilton Equation is expressed as follows:

$$CO = \frac{Si \cdot Ci \cdot (Tb - Ti) \, Vi}{Sb \cdot Cb \cdot \int_0^\infty \Delta Tb \, dt}$$

where CO: the cardiac output, Si: the specific gravity of the injectate, Ci: the specific heat of the injectate, Vi: the injectate volume, Ti: the injectate temperature, Tb: the temperature of the blood, Sb: the specific gravity of the blood, Cb: the specific heat of the blood. The aforementioned equation is also expressed as follows:

$$CO = A \cdot \frac{(Tb - Ti)}{\int_0^\infty \Delta Tb \, dt}$$

where $$A = \frac{Si \cdot Ci \cdot Vi}{Sb \cdot Cb}$$

Figure 12:
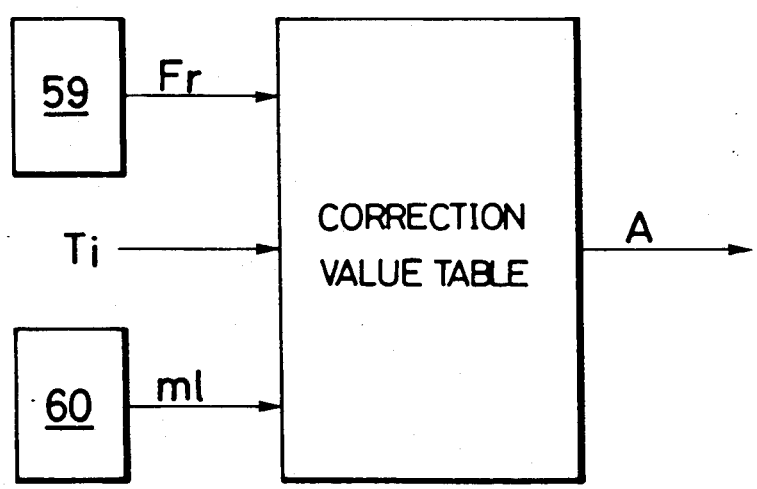
FIG. 12 shows a table for storing correction constant A.

In this constant A, whereas Si, Sb, Cb and Ci are fixed values, the volume of injectate Vi may vary because part of the indicator remains within the catheter when it is injected into the blood vessel after the temperature thereof has been set to a predetermined value. In other words, Vi is a nominal value. Further, residual indicator in the catheter makes the heating value of the injectate into the blood vessel obscure. The absolute heating value also depends on the injectate temperature. In consequence, conventionally, the correction constant A' is obtained by referring to a table which is created through the experiments using the catheter size, the volume Vi of indicator and so on. However, in this embodiment, in order to improve the operability, the correction constant A' is (FIG. 12) stored in the ROM 131 in a tabulated form. When one correction constant A' is drawn from the table, the outer diameter Fr of the catheter 4 and the nominal volume ml of injectate, which are input from the switches 59 and 60, are used as the address data, as shown in FIG. 12. More specifically, the CPU 133 reads the values set in the switches 59 and 60 through the I/O port 134, and converts these values and the temperature Ti of the indicator into the address data with which it addresses the ROM 131. The correction constant data contained in the table is obtained in the actual measurements which were conducted using the catheter having various sizes and various volumes of indicator. If the size of the actually employed catheter and the injectate volume correspond to no value contained in the table, a correction constant A' is obtained by the linear interpolation using the values existing in the table which are close to the above-described values.

After the integration, $\Sigma \Delta Tb$, has been completed in step S68, the correction constant A' is read out from the table (FIG. 12) stored in the ROM 131 in step S71 in the manner described above using the outer diameter Fr of the catheter and the injectate volume ml, which are input by means of the switches 59 and 60. In step S71, the initial cardiac output COo is calculated on the basis of the Stewart/Hamilton Equation described above. Thereafter in step S72, the parameter S, which is required to calculate the continuous cardiac output Cox, is calculated. In step S73, the thus-obtained values are output to the plotter in the form shown in, for example, FIGS. 4 and 5.

Continuous Measurement of COx

First, the principle on the basis of which COx can be continuously calculated will be described below. Where Rt is the resistance of the thermistor 1, and Ic is the current supplied to the thermistor 1 by the constant-current circuit 111, the quantity of heat generated in unit time by the heated thermistor 1 is expressed as follows:

$$Ic^2 \cdot Rt$$

When the heated thermistor 1 is placed in the blood which flows at a velocity of V, the thermistor 1 loses heat in accordance with the blood flow velocity V. The quantity of heat which is lost from the thermistor 1 in accordance with the blood flow is expressed as follows:

$$K \cdot V \cdot (Tt - Tb)$$

where Tb is the temperature of the blood, Tt is the temperature of the heated thermistor, and K is the constant of proportion. The temperature of the thermistor 1 is kept at a value at which the quantity of heat generated by the heated thermistor is equal to that lost from the thermistor. This temperature is called heat balanced temperature. This is expressed as follows:

$$Ic^2 \cdot Rt = K \cdot V \cdot (Tt - Tb) \qquad (2)$$

The equation (2) results in the following equation (3):

$$V = (1/K)(Ic^2 \cdot Rt)/(Tt - Tb) \qquad (3)$$

More specifically, the blood flow velocity V is obtained from the data Rt and Tt obtained from the thermistor 1 and the blood temperature Tb obtained from the thermistor 2. Since the thermistor 1 is driven by the constant-current circuit 111, the potential Eo between the two ends of the lead for the thermistor 1 may be detected in place of the resistance of the thermistor 1. This detection is described in detail in the specification of Japanese Patent Laid-Open No. 61-125329. In this embodiment, the constant-current value Ic is obtained by detecting the current in the constant-current circuit 111. However, it may be stored within the ROM 131 as the constant term, like the constant of proportion K.

The initial cardiac output COo and the initial blood flow velocity Vo has the relationship expressed by the following equation:

$$COo = s \cdot Vo \qquad (4)$$

where s is the cross-sectional area of the blood vessel.

Hence, the cross-sectional area s of the blood vessel is obtained from the initial cardiac output COo and the initial blood flow velocity V by using Equation (4), and the obtained s is held within the measuring/recording circuit 130 as a parameter. Once the parameter s has been obtained, continuous cardiac output COx can be obtained by the CPU 133 by multiplying the continuously measured blood flow velocity Vx by the parameter S. This will be expressed as follows:

$$COx = s \cdot Vx = (s/K) \cdot (Ic^2 \cdot Rt)/(Tt - Tb) \qquad (5)$$

FIG. 14A shows in detail the processing executed in step S72 in FIG. 13 in which the parameter s is calculated. First, an instruction of heating the thermistor 1 is given to the local CPU 105 through the optical communication path in step S110 shown in FIG. 14A. In step S112, the thermistor 1 being heat balanced is awaited. Soon, Tt, Rt, and Tb arrive from the local CPU, the arrived data being stored in sequence in the RAM 132 by the procedure shown in FIG. 11. In consequence, in step S113, the data stored in the RAM 132 is accessed by means of the RC pointer 161 in accordance with the time t. In step S114, the initial blood flow velocity Vo is calculated on the basis of Equation (3), and the parameter s is then obtained in step S115 on the basis of Equation (4) utilizing the relationship between the initial cardiac output COo and the blood flow velocity Vo. Thus, preparation for the continuous measurement of COx is completed.

Figure 14B:
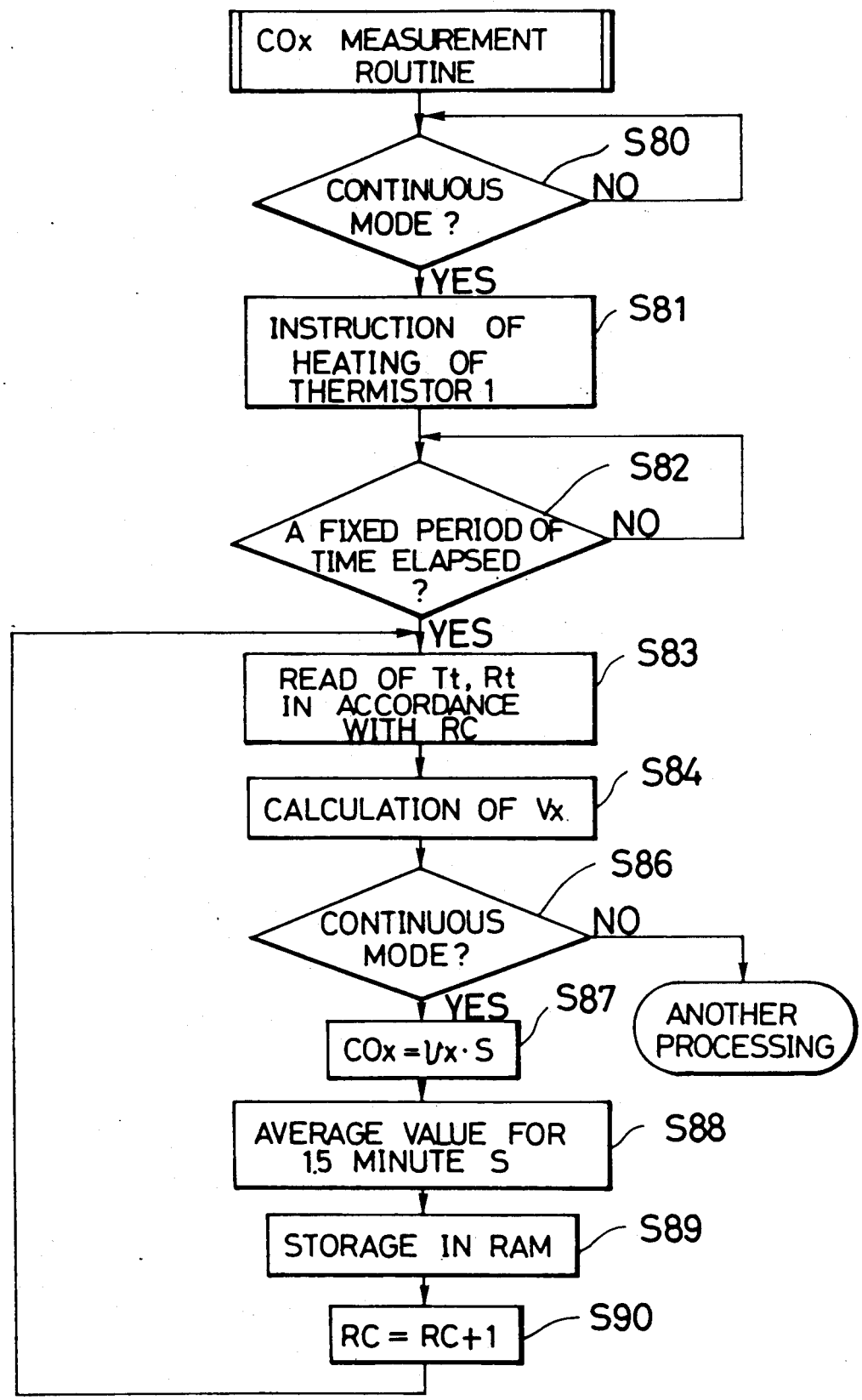
Figure 16:
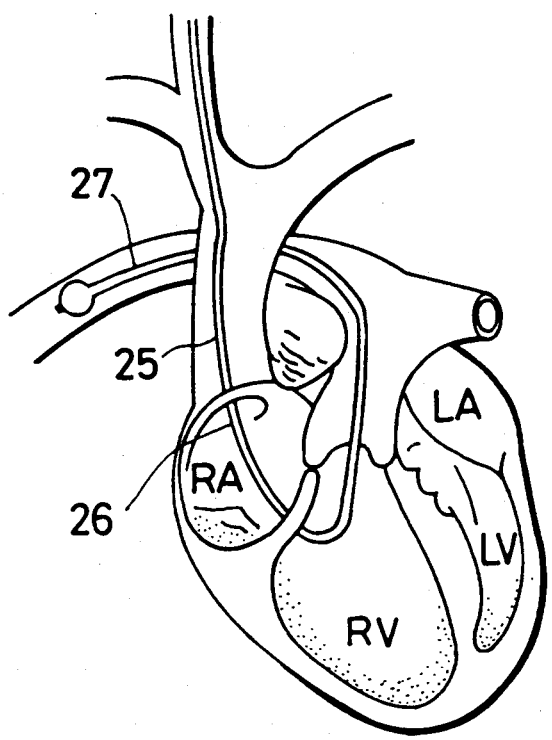
FIGS. 16 and 17 illustrate the principle of the conventional measurement of the cardiac output by the thermal dilution method.

Next, the calculation procedure of COx will be described in detail with reference to FIG. 14B. This calculation is performed after the initial cardiac output COo and the parameter s have been obtained.

First, it is determined in step S80 whether or not the measuring apparatus 100 is in the continuous mode. This is achieved by pressing the CONTINUOUS switch 64. If the measuring apparatus 100 is in the continuous mode, an instruction of heating the thermistor 1 is given to the local CPU 105 through the optical communication path in step S81. In step S82, the thermistor 1 being heat balanced is awaited. Soon, Tt, Rt and Tb arrive from the local CPU, the arrived data being stored in sequence within the RAM 132 by the procedure shown in FIG. 11. In consequence, the data stored in the RAM 132 is accessed by means of the RC pointer 161 in accordance with the time t. In step S84, the blood flow velocity Vx is calculated on the basis of Equation (3).

It is determined in step S86 whether or not the measuring apparatus 100 is still in the continuous mode. This is done because the parameter s representing the cross-sectional area of the blood vessel generally changes with time, making it impossible for an accurate cardiac output to be obtained using the parameter s held. Hence, the initial cardiac output CO is measured by the thermal dilution method at adequate intervals so that it can be used in a subsequent continuous measurement of COx.

If the measuring apparatus is still in the continuous mode, the processing goes to step S87 where $$COx = Vx \cdot S$$

is calculated. In step S88, the average values of Vx and COx in 1.5 minutes are operated, which will be used in the reproduction of data obtained over 12 hours (FIG. 8). The values obtained in step S88 are stored in the area 132c in the RAM 132. Thereafter, in step S90, the RC pointer is incremented by one for the subsequent operation of COx.

Thus, Cox can be continuously operated each time Tt, Rt, and Tb arrive from the local CPU, which means that Cox can be measured by measuring the blood flow velocity Vx.

Recording of Data

The measuring apparatus 100 has the continuous recording function (which is performed by pressing the switch 56) in which the measured value is output to the plotter 50 while it is being continuously obtained, the reproduction function (performed by pressing the switch 55) in which the measured values obtained over 30 minutes are output to the plotter 50, and the record output function (performed by pressing the switch 54) in which the measured values obtained over 12 hours (the average values in each 3 minutes) are output to the plotter 50, in addition to the thermal dilution curve recording function shown in FIG. 4 and the thermal dilution value recording function shown in FIG. 5.

In the continuous recording and reproduction, the recording paper is fed at a speed of 10 m/min, as shown in FIG. 6, or at a speed of 20 ms/hour, as shown in FIG. 7.

FIG. 8 shows an example of the record. In this record, CO (=COx) and the blood temperature BT (=Tb) are graphically recorded for each 3 hours.

The above-described recordings are performed in the continuous mode (while the CONTINUOUS indicator 64 is lighting up). This means that the reception of data from the local CPU 105 and the operation/storage of COx have to be performed parallel to the output of data to the plotter 50. In order to accomplish this, the PC pointer is used when the data in the RAM 132 is accessed and output to the plotter 50, the SC pointer 160 is used to fetch the data, and the RC pointer 160 is used for operation/storage.

Substitute of Temperature of Indicator

Since the indicator to be injected into the blood vessel from the catheter 4 is contained in an ice-cooled container, the injectate temperature is determined by the temperature of the container. In consequence, in a case where the temperature of the container is a known value (for example, zero), that temperature may substitute for that of the indicator.

Hence, when it is determined that the temperature probe 12 is not connected, the temperature set by means of the switch 75 is regarded as the injectate temperature Ti and is used in the calculation of the initial cardiac output COo. In order to accomplish this, the injectate temperature detecting circuit 102 detects that the current that flows in the thermistor 12a connected to the constant voltage circuit 101 is zero, and sends Ei corresponding to the zero current to the local CPU 105. The local CPU 105 sends a corresponding signal to the main CPU 133. Alternatively, the CPU 105 converts Ei corresponding to the zero current into an impossible temperature value Ti, and sends the resultant signal to the main CPU 133. Thus, the CPU 133 detects the non-connection of the temperature probe 12.

FIG. 15 is a flowchart of this control procedure. In place of the processing of step S52 shown in FIG. 13 where the main CPU 133 reads out Ti from the RAM 132, it is determined in step S100 whether or not Ti received from the local CPU 105 represents non-connection of the probe 12. If Ti represents connection, Ti stored in the RAM 132 is fetched in the CPU 133 in step S101. If Ti represents non-connection, the data set by means of the switch 75 is fetched as Ti in step S102.

Measurement of Relative Change in Cardiac Output

In the above-described embodiment, the initial cardiac output COo is actually obtained by the thermal dilution method, and the parameter s is then obtained from the relation between the COo and the initial blood flow velocity Vo. Thereafter, the cardiac output COx is continuously obtained by measuring the blood flow velocity Vx at an arbitrary time. In other words, $$COx \propto Vx,$$

and changes in Vx reflects relative changes in COx. Hence, recording of changes in Vx means recording of relative changes in COx. In a case where the measurement is conducted on the same examinee by the operator who is skillful in the measurement, it is possible to estimate the initial cardiac output CO. Hence, in this embodiment, the rough cardiac output CO may be input from the switch 62 as "the initial CAL value" (=COo), the parameter s being operated within the measuring apparatus on the basis of this COo. This omits the measurement of the initial cardiac output COo by the thermal dilution method.

Results of the Experiments

Figure 19:
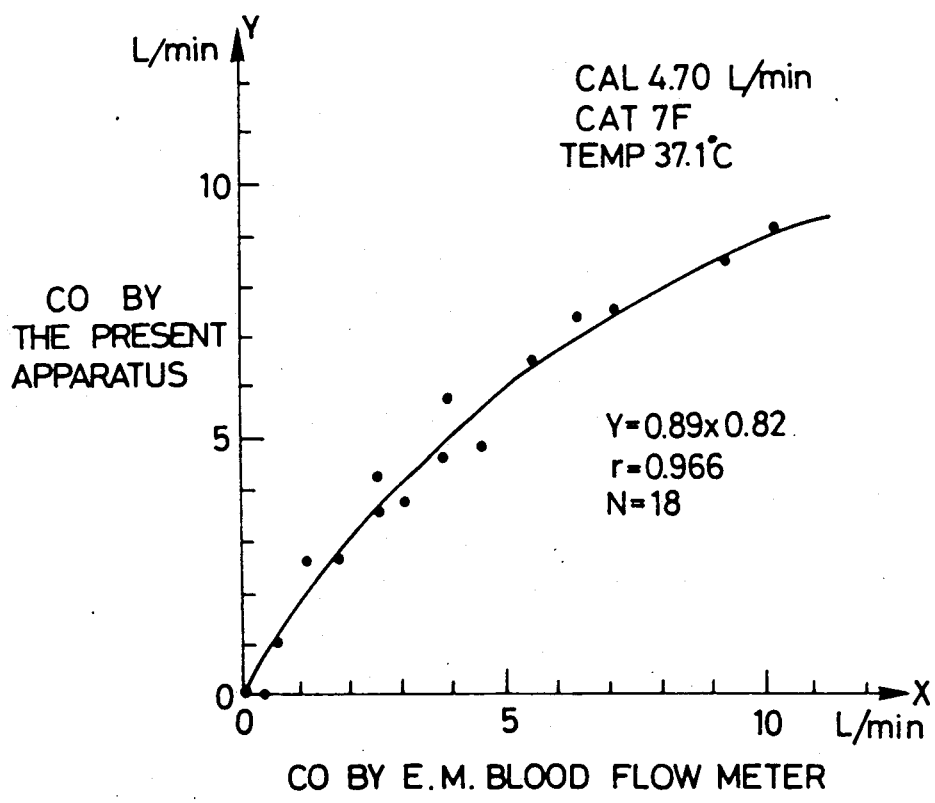
FIG. 19 is a graph, showing the results of the experiment conducted using the measuring apparatus of FIG. 1.

A measuring system was formed by connecting the catheter 4 shown in FIG. 2A to the measuring apparatus shown in FIGS. 9A and 9B. Two experiments were conducted using this measuring system. In one experiment, the measuring system was applied to the circulatory model circuit. The other was the experiment on the dog which was the 15 Kg adult mongrel under an anesthetic. The model circuit was constructed by a constant-temperature tank, a pump and so on. In the latter experiment on the animal, the catheter 4 which was introduced from the right internal jugular vein was advanced into the pulmonary artery. Comparison example was obtained using the electromagnetic blood flowmeter. FIG. 19 shows the results of the measurement obtained in the circulatory model circuit. In the graph shown in FIG. 19, in which the axis of the abscissa represents the cardiac output (unit L/min) obtained by using the electromagnetic blood flowmeter, and the axis of the ordinate represents the cardiac output obtained by the measuring system, the correlation between the two types of cardiac outputs expressed by the following equation was obtained:

$$Y = 0.89 X + 0.82$$

The correlation coefficient r was 0.966 (the number of samples = 18). On the other hand, in the experiment on the animal, the correlation obtained was $$Y = 1.48 X - 0.78, \text{ and}$$

the correlation coefficient r was 0.944 (the number of samples = 29). In both cases, excellent results could be obtained in the region of 0 to 4 L/min. Furthermore, good results could be recognized in a high cardiac output region of 0 to 10 L/min, as shown in FIG. 19. It is considered that the good results was ensured in the high cardiac output region of 0 to 10 L/min because of the provision of the 14-bit A/D converter 104.

Application of the Apparatus to Another Dilution Methods

In the above-described continuous cardiac output measurement, once the initial cardiac output CO is measured by some method, the parameter s is measured from the obtained initial cardiac output. Thereafter, a cardiac output COx can be continuously obtained by measuring a blood flow velocity Vx. Thus, the present invention can be applied to the dilution methods other than the thermal dilution method, e.g., the dye dilution method or the electrolyte dilution method. In the dye dilution method, initial cardiac output CO is obtained by measuring the change in the illuminance in, for example, an earlobe which occurs in accordance with the amount of dye in the blood. In the electrolyte dilution method, the initial cardiac output CO is obtained by measuring the change in the resistance in the blood by means of two electrodes provided in the catheter.

More specifically, the function of inputting the data (e.g., Fr or ml) upon which the correction constant A' is based, which is described in Item (1), can be applied to any type of indicator dilution method which employs a catheter. Furthermore, the automatic measurement starting function described in Item (2) can be applied to the measurement of a change in the illuminance or the resistance. Further, the continuous cardiac output measuring function described in Item (4) can be applied to the calculation of COx from the parameter s obtained on the basis of the initial cardiac output COo obtained by any indicator dilution method and from the blood flow velocity Vx obtained at an arbitrary time.

Connection/non-connection of the temperature probe 12 may also be detected by the following mechanism: a protrusion is provided at the portion of the measuring apparatus body to which the connector 16 of the probe is connected in such a manner that it is urged. When the connector 16 is connected to this protrusion, the protrusion retreats, by means of which the end of the protrusion supplies, for example, an earth signal, to the measuring circuit 120. The measuring circuit 120 determines connection/non-connection of the probe 12 by the presence and absence of the earth signal. The protrusion is electrically isolated from the measuring circuit 120 except for its end, so as to allow the measuring circuit 120 to be electrically isolated.

In the above-described embodiment, the blood flow velocity is measured by the thermistor 1 which detects the voltage representing the heat balance. i.e., change in the resistance of the thermistor, which is obtained when a constant current flows therein. However, it may also be measured by measuring the current required to maintain the difference in the temperature of the blood and that of the thermistor constant. More specifically, the temperature of the thermistor is maintained at 45° C. which is the upper limit of the temperatures which do not affect the human body, and the current required to maintain the temperature of the thermistor at that value is measured. Blood flow velocity sensors other than the thermistor may also be used.

Obvious modifications and alterations of the above-described embodiment will occur to those skilled in the art upon reading and understanding of this specification. The intention is to include all such modifications and alterations insofar as they come within the scope of the appended claims.

What is claimed is:

1. An apparatus for measuring cardiac output by a thermal dilution method, comprising:
   injection means for injecting an indicator into a blood vessel;
   data setting means for manually inputting indicator data on the indicator prior to injection into the blood vessel;
   measuring means for measuring injectate data on the indicator prior to injection into the blood vessel;
   fault detection means for detecting that said measuring means is inoperative;
   blood data detection means for detecting blood data on blood diluted by the indicator injected into the blood vessel;

integration means for integrating the blood data obtained by said blood data detection means to produce an integral value;

selection means for selecting the indicator data set by said setting means when said fault detection means detects that said measuring means is inoperative and otherwise selecting the injectate data, as selected data; and cardiac output indication means for indicating cardiac output from the selected data and the integral value.

2. A cardiac output measuring apparatus according to claim 1, wherein said measuring means includes a measuring probe connected to said cardiac output indication means, wherein said fault detection means includes non-connection detection means for detecting non-connection of said measuring probe to said cardiac output indication means, and wherein said selection means selects the indicator data as the selected data only when said non-connection detection means detects non-connection.

3. A cardiac output measuring apparatus according to claim 1, wherein said indicator data represents the temperature of the indicator.

4. A cardiac output measuring apparatus according to claim 1, wherein said data setting means includes numeric input keys.

5. An apparatus for measuring cardiac output by a thermal dilution method, having an automatic measurement starting function, comprising:

blood data detecting means for outputting blood data on blood diluted by an indicator injected into a blood vessel;

variation detection means for detecting variation in the blood data;

comparison means for comparing the variation in the blood data with a predetermined value to determine whether the variation is at least as large as the predetermined value;

integration means for performing integration of the blood data starting at a time subsequent to said comparison determining that the variation is at least as large as the predetermined value;

integration period determination means for determining an integration period of the integration performed by said integration means in dependence upon the predetermined value and a peak value of the variation in the blood data detected by said variation detection means;

integration stopping means for stopping the integration of the blood data at the end of the integration period; and cardiac output operating means for indicating a cardiac output from the integral value of the integration performed by said integration means.

6. A cardiac output measuring apparatus according to claim 5, wherein said blood data detecting means includes a temperature sensor, and wherein the blood data represents data on the temperature of the blood diluted by the indicator injected into the blood vessel.

7. A cardiac output measuring apparatus according to claim 5, wherein said integration means includes:

determination means for determining reference data in dependence upon the variation of the blood before said comparison means performs the comparing;

operation means for integrating a difference between the blood data and the reference data each integration period; and stoppage means for stopping the integration when the blood data substantially coincides with the reference data.

8. A cardiac output measuring apparatus according to claim 5, wherein said integration means includes:

determination means for determining reference data in dependence upon the variation of the blood before said comparison means performs the comparing;

operation means for integrating a difference between the blood data and the reference data each integration period; and detection means for detecting a peak value of the difference, and wherein said integration period determination means includes means for obtaining the integration period for continuing the integration in dependence upon the peak value.

9. A cardiac output measuring apparatus according to claim 5, wherein said indicator contains a dye, wherein said blood data detecting means includes a sensor for detecting the concentration of the dye in the blood as illuminance, and wherein said blood data represents illuminance data.

10. A cardiac output measuring apparatus according to claim 5, wherein said indicator contains an electrolyte, wherein said blood data detection means includes a resistance sensor for detecting a resistance of the electrolyte in the blood, and wherein said blood data represents a resistance.

11. A cardiac output measuring apparatus, comprising:

initial cardiac output measuring means for performing measurement of an initial cardiac output using a dilution method in a blood vessel at least once to obtain an initial cardiac output indication;

blood flow velocity measuring means for measuring initial blood flow velocity data and subsequent blood flow velocity data nearby a portion of the blood vessel used by said initial cardiac output measuring means;

means for independently generating a first memory pointer and a second memory pointer;

memory means for storing the initial blood flow velocity data and the subsequent blood flow velocity data measured by said blood flow velocity measuring means, at a location indicated by said first memory pointer;

data retrieving means for retrieving the initial blood flow velocity data and the subsequent blood flow velocity data using said second memory pointer;

function operation means for generating a function representing a relation between the initial cardiac output indication obtained in dependence upon the dilution method and the initial blood flow velocity data obtained when the initial cardiac output is measured;

cardiac output operation means for continuously indicating cardiac output repeatedly updated in dependence upon the function and the subsequent blood flow velocity data retrieved by said data retrieving means; and recording means for visually and retroactively recording the cardiac output indicated by said cardiac output operation means.

12. A cardiac output measuring apparatus according to claim 11,
wherein the dilution method is a thermal dilution method,
wherein said initial cardiac output measuring means includes:
a catheter having an opening through which an indicator is injected into the blood vessel;
a first thermistor for measuring blood temperature data of blood diluted by the indicator downstream of said catheter in the blood vessel; and
integrating means for integrating the blood temperature data detected by said thermistor, and
wherein said blood flow velocity measuring means includes a second thermistor of a self-heating type, provided nearby said first thermistor of said catheter.

13. A cardiac output measuring apparatus according to claim 12, characterized by the inclusion of a first microprocessor for collecting data, a second microprocessor for processing data, and a communication means for exchanging data between said two microprocessors, wherein said first microprocessor collects the blood temperature data detected by said first thermistor and heat balanced temperature data detected by said second thermistor, and sends them to said second microprocessor by means of said communication means, and wherein said second microprocessor processes the data collected and thereby operates said initial cardiac output and said function.

14. A cardiac output measuring apparatus according to claim 11,
wherein said initial cardiac output operation means includes:
compression means for compressing a plurality of cardiac outputs detected within a predetermined period of time, and
a memory for storing the cardiac outputs compressed by said compression means, and
wherein said recording means is capable of recording the cardiac outputs compressed and stored in said memory.

15. An apparatus for continuously measuring relative changes in a cardiac output, comprising:
blood flow velocity measuring means for measuring a blood flow velocity in a blood vessel;
input means for inputting; a cross-sectional area of the blood vessel where the blood flow velocity is measured; and
cardiac output operation means for continuously indicating relative changes in the cardiac output which occur over time in dependence upon the cross-sectional area of the blood vessel and the blood flow velocity measured by said blood flow velocity measuring means.

16. A measuring method for measuring cardiac output using a thermal dilution method, comprising the steps of:
(a) storing, into a memory table prior to measuring the cardiac output, correction data on heat capacity of an indicator;
(b) injecting the indicator into a blood vessel;
(c) detecting blood data on blood diluted by the indicator injected in step (b);
(d) retrieving the correction data from the memory table in dependence upon heat capacity data for the indicator;
(e) calculating a time integration value using the blood data; and
(f) indicating a cardiac output in dependence upon the time integration value and the correction data, in accordance with the thermal dilution method.

17. A measuring method according to claim 16, wherein said blood data represents temperature of the blood.

18. A measuring method according to claim 16, wherein said heat capacity data represents volume of the indicator injected in step (b).

19. A measuring method according to claim 16,
wherein said injecting in step (b) injects the indicator into the blood vessel via a catheter having an outer diameter, and
wherein the heat capacity data represents the outer diameter of the catheter.

20. A measuring method according to claim 16,
wherein said injecting in step (b) injects the indicator into the blood vessel via a catheter, and
wherein said heat capacity data represents temperature of the indicator.

21. A measuring method according to claim 16, further comprising the step of (g) inputting the heat capacity data of the indicator via numeric input keys.

* * * * *